(12) United States Patent
Wham et al.

(10) Patent No.: US 7,722,601 B2
(45) Date of Patent: *May 25, 2010

(54) METHOD AND SYSTEM FOR PROGRAMMING AND CONTROLLING AN ELECTROSURGICAL GENERATOR SYSTEM

(75) Inventors: Robert H. Wham, Boulder, CO (US); Thomas A. Sturm, Erie, CO (US); William D. Faulkner, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 741 days.

This patent is subject to a terminal disclaimer.

(21) Appl. No.: 10/554,837

(22) PCT Filed: Apr. 30, 2004

(86) PCT No.: PCT/US2004/013443

§ 371 (c)(1), (2), (4) Date: Dec. 19, 2006

(87) PCT Pub. No.: WO2004/098385

PCT Pub. Date: Nov. 18, 2004

(65) Prior Publication Data

US 2007/0093800 A1      Apr. 26, 2007

Related U.S. Application Data

(60) Provisional application No. 60/466,954, filed on May 1, 2003.

(51) Int. Cl.
*A61B 18/04* (2006.01)
(52) U.S. Cl. .......................... 606/34; 606/35
(58) Field of Classification Search ............. 606/32–34, 606/37–42
See application file for complete search history.

(56) References Cited

U.S. PATENT DOCUMENTS 1,787,709 A    1/1931   Wappler (Continued)

FOREIGN PATENT DOCUMENTS

DE           179607         3/1905

(Continued)

OTHER PUBLICATIONS

International Search Report EP 07008207.8 dated Sep. 5, 2007.

(Continued)

*Primary Examiner*—Linda C Dvorak
*Assistant Examiner*—Amanda Scott

(57) ABSTRACT

A method and system are disclosed enabling configuration of a control system for an electrosurgical generator system for creating new surgical applications without changing the underlying software system. The system includes an outer loop controller for generating a control signal in accordance with at least a first subset of sensor data from at least one sensor; an inner loop controller for generating a setpoint control signal which is provided to an RF stage in accordance with at least the control signal generated by the outer loop controller and a second subset of sensor data from the at least one sensor; and a configuration controller for generating configuration data and providing first and second configuration data sets of the configuration data to the inner loop and outer loop controllers, respectively, for configuration thereof to provide a type of control selectable from a variety of types of control.

8 Claims, 4 Drawing Sheets

U.S. PATENT DOCUMENTS

| | | |
|---|---|---|
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Humio |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A * | 3/1980 | Belt et al. .................... 606/37 |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,586,120 A | 4/1986 | Malik et al. |
| 4,590,934 A | 5/1986 | Malis et al. |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |

| | | | | | | |
|---|---|---|---|---|---|---|
| 4,657,015 A | 4/1987 | Irnich | | 5,318,563 A | 6/1994 | Malis et al. |
| 4,658,815 A | 4/1987 | Farin et al. | | 5,323,778 A | 6/1994 | Kandarpa et al. |
| 4,658,819 A | 4/1987 | Harris et al. | | 5,324,283 A | 6/1994 | Heckele |
| 4,658,820 A | 4/1987 | Klicek | | 5,330,518 A | 7/1994 | Neilson et al. |
| 4,662,383 A | 5/1987 | Sogawa et al. | | 5,334,183 A | 8/1994 | Wuchinich |
| 4,691,703 A | 9/1987 | Auth et al. | | 5,334,193 A | 8/1994 | Nardella |
| 4,712,559 A | 12/1987 | Turner | | 5,341,807 A | 8/1994 | Nardella |
| 4,727,874 A | 3/1988 | Bowers et al. | | 5,342,356 A | 8/1994 | Ellman |
| 4,735,204 A | 4/1988 | Sussman et al. | | 5,342,357 A | 8/1994 | Nardella |
| 4,739,759 A | 4/1988 | Rexroth et al. | | 5,342,409 A | 8/1994 | Mullett |
| 4,741,334 A | 5/1988 | Irnich | | 5,348,554 A | 9/1994 | Imran et al. |
| 4,754,757 A | 7/1988 | Feucht | | 5,370,645 A | 12/1994 | Klicek et al. |
| 4,788,634 A | 11/1988 | Schlecht et al. | | 5,370,672 A | 12/1994 | Fowler et al. |
| 4,805,621 A | 2/1989 | Heinze et al. | | 5,370,675 A | 12/1994 | Edwards et al. |
| 4,818,954 A | 4/1989 | Flachenecker et al. | | 5,372,596 A | 12/1994 | Klicek et al. |
| 4,827,911 A | 5/1989 | Broadwin et al. | | 5,383,874 A | 1/1995 | Jackson |
| 4,827,927 A | 5/1989 | Newton | | 5,383,876 A | 1/1995 | Nardella |
| 4,832,024 A | 5/1989 | Boussignac et al. | | 5,383,917 A | 1/1995 | Desai et al. |
| 4,848,335 A | 7/1989 | Manes | | 5,385,148 A | 1/1995 | Lesh et al. |
| 4,848,355 A | 7/1989 | Nakamura et al. | | 5,396,062 A | 3/1995 | Eisentraut et al. |
| 4,860,745 A | 8/1989 | Farin et al. | | 5,400,267 A | 3/1995 | Denen et al. |
| 4,862,889 A | 9/1989 | Feucht | | 5,403,311 A | 4/1995 | Abele et al. |
| 4,880,719 A | 11/1989 | Murofushi et al. | | 5,403,312 A | 4/1995 | Yates et al. |
| 4,887,199 A | 12/1989 | Whittle | | 5,409,000 A | 4/1995 | Imran |
| 4,890,610 A | 1/1990 | Kirwan et al. | | 5,409,006 A | 4/1995 | Buchholtz et al. |
| 4,903,696 A | 2/1990 | Stasz et al. | | 5,409,485 A | 4/1995 | Suda |
| 4,907,589 A | 3/1990 | Cosman | | 5,413,573 A | 5/1995 | Koivukangas |
| 4,922,210 A | 5/1990 | Flachenecker et al. | | 5,414,238 A | 5/1995 | Steigerwald et al. |
| 4,931,047 A | 6/1990 | Broadwin et al. | | 5,417,719 A | 5/1995 | Hull et al. |
| 4,931,717 A | 6/1990 | Gray et al. | | 5,422,567 A | 6/1995 | Matsunaga |
| 4,938,761 A | 7/1990 | Ensslin | | 5,423,808 A | 6/1995 | Edwards et al. |
| 4,942,313 A | 7/1990 | Kinzel | | 5,423,809 A | 6/1995 | Klicek |
| 4,959,606 A | 9/1990 | Forge | | 5,423,810 A | 6/1995 | Goble et al. |
| 4,961,047 A | 10/1990 | Carder | | 5,425,704 A | 6/1995 | Sakurai et al. |
| 4,961,435 A | 10/1990 | Kitagawa et al. | | 5,430,434 A | 7/1995 | Lederer et al. |
| 4,966,597 A | 10/1990 | Cosman | | 5,432,459 A | 7/1995 | Thompson |
| RE33,420 E | 11/1990 | Sussman | | 5,433,739 A | 7/1995 | Sluijter et al. |
| 4,969,885 A | 11/1990 | Farin | | 5,434,398 A | 7/1995 | Goldberg |
| 4,992,719 A | 2/1991 | Harvey | | 5,436,566 A | 7/1995 | Thompson |
| 4,993,430 A | 2/1991 | Shimoyama et al. | | 5,438,302 A | 8/1995 | Goble |
| 4,995,877 A | 2/1991 | Ams et al. | | 5,443,463 A | 8/1995 | Stern et al. |
| 5,015,227 A | 5/1991 | Broadwin et al. | | 5,445,635 A | 8/1995 | Denen |
| 5,019,176 A | 5/1991 | Brandhorst, Jr. | | 5,451,224 A | 9/1995 | Goble et al. |
| 5,024,668 A | 6/1991 | Peters et al. | | 5,458,597 A | 10/1995 | Edwards et al. |
| 5,029,588 A | 7/1991 | Yock et al. | | 5,462,521 A | 10/1995 | Brucker et al. |
| 5,087,257 A | 2/1992 | Farin | | 5,472,441 A | 12/1995 | Edwards et al. |
| 5,099,840 A | 3/1992 | Goble et al. | | 5,472,443 A | 12/1995 | Cordis et al. |
| 5,103,804 A | 4/1992 | Abele et al. | | 5,478,303 A | 12/1995 | Folry-Nolan et al. |
| 5,108,389 A | 4/1992 | Cosmescu | | 5,480,399 A | 1/1996 | Hebborn |
| 5,108,391 A | 4/1992 | Flachenecker et al. | | 5,483,952 A | 1/1996 | Aranyi |
| 5,122,137 A | 6/1992 | Lennox | | 5,490,850 A | 2/1996 | Ellman et al. |
| 5,133,711 A | 7/1992 | Hagen | | 5,496,312 A | 3/1996 | Klicek |
| 5,151,102 A | 9/1992 | Kamiyama et al. | | 5,496,313 A | 3/1996 | Gentelia et al. |
| 5,152,762 A | 10/1992 | McElhenney | | 5,500,012 A | 3/1996 | Brucker et al. |
| 5,157,603 A | 10/1992 | Scheller et al. | | 5,500,616 A | 3/1996 | Ochi |
| 5,160,334 A | 11/1992 | Billings et al. | | 5,514,129 A | 5/1996 | Smith |
| 5,162,217 A | 11/1992 | Hartman | | 5,520,684 A | 5/1996 | Imran |
| 5,167,658 A | 12/1992 | Ensslin | | 5,531,774 A | 7/1996 | Schulman et al. |
| 5,190,517 A | 3/1993 | Zieve et al. | | 5,534,018 A | 7/1996 | Wahlstrand et al. |
| 5,196,008 A | 3/1993 | Kuenecke | | 5,536,267 A | 7/1996 | Edwards et al. |
| 5,196,009 A | 3/1993 | Kirwan, Jr. | | 5,540,681 A * | 7/1996 | Strul et al. .................. 606/34 |
| 5,201,900 A | 4/1993 | Nardella | | 5,540,683 A | 7/1996 | Ichikawa |
| 5,207,691 A | 5/1993 | Nardella | | 5,540,684 A | 7/1996 | Hassler, Jr. |
| 5,230,623 A | 7/1993 | Guthrie et al. | | 5,540,724 A | 7/1996 | Cox |
| 5,233,515 A | 8/1993 | Cosman | | 5,556,396 A | 9/1996 | Cohen et al. |
| 5,249,121 A | 9/1993 | Baum et al. | | 5,558,671 A | 9/1996 | Yates |
| 5,254,117 A | 10/1993 | Rigby et al. | | 5,569,242 A | 10/1996 | Lax et al. |
| RE34,432 E | 11/1993 | Bertrand | | 5,571,147 A | 11/1996 | Sluijter et al. |
| 5,267,994 A | 12/1993 | Gentelia et al. | | 5,573,533 A | 11/1996 | Strul |
| 5,267,997 A | 12/1993 | Farin | | 5,584,830 A | 12/1996 | Ladd et al. |
| 5,281,213 A | 1/1994 | Milder et al. | | 5,588,432 A | 12/1996 | Crowley |
| 5,300,068 A | 4/1994 | Rosar et al. | | 5,594,636 A | 1/1997 | Schauder |
| 5,300,070 A | 4/1994 | Gentelia | | 5,596,466 A | 1/1997 | Ochi |

| Patent | Date | Inventor | Patent | Date | Inventor |
|---|---|---|---|---|---|
| 5,599,344 A | 2/1997 | Paterson | 6,010,499 A | 1/2000 | Cobb |
| 5,599,345 A | 2/1997 | Edwards et al. | 6,014,581 A | 1/2000 | Whayne et al. |
| 5,599,348 A | 2/1997 | Gentelia et al. | 6,033,399 A | 3/2000 | Gines |
| 5,605,150 A | 2/1997 | Radons et al. | 6,044,283 A | 3/2000 | Fein et al. |
| 5,613,966 A | 3/1997 | Makower et al. | 6,053,910 A | 4/2000 | Fleenor |
| 5,613,996 A | 3/1997 | Lindsay | 6,053,912 A | 4/2000 | Panescu et al. |
| 5,625,370 A | 4/1997 | D'Hont | 6,055,458 A | 4/2000 | Cochran et al. |
| 5,626,575 A * | 5/1997 | Crenner ............ 606/34 | 6,056,745 A | 5/2000 | Panescu et al. |
| 5,628,745 A | 5/1997 | Bek | 6,056,746 A | 5/2000 | Goble et al. |
| 5,643,330 A | 7/1997 | Holsheimer et al. | 6,063,075 A | 5/2000 | Mihori |
| 5,647,869 A | 7/1997 | Goble et al. | 6,063,078 A | 5/2000 | Wittkampf |
| 5,647,871 A | 7/1997 | Levine et al. | 6,068,627 A | 5/2000 | Orszulak et al. |
| 5,651,780 A | 7/1997 | Jackson et al. | 6,074,386 A | 6/2000 | Goble et al. |
| 5,658,322 A | 8/1997 | Fleming | 6,074,388 A | 6/2000 | Tockweiler et al. |
| 5,660,567 A | 8/1997 | Nierlich et al. | 6,080,149 A | 6/2000 | Huang et al. |
| 5,674,217 A | 10/1997 | Wahlstrom et al. | 6,093,186 A | 7/2000 | Goble |
| 5,685,840 A | 11/1997 | Schechter et al. | 6,102,497 A | 8/2000 | Ehr et al. |
| 5,688,267 A * | 11/1997 | Panescu et al. ............ 606/41 | RE36,871 E | 9/2000 | Epstein |
| 5,690,692 A | 11/1997 | Fleming | 6,113,591 A | 9/2000 | Whayne et al. |
| 5,693,042 A | 12/1997 | Bioarski et al. | 6,113,596 A | 9/2000 | Hooven |
| 5,694,304 A | 12/1997 | Telefus et al. | 6,123,702 A | 9/2000 | Swanson et al. |
| 5,695,494 A | 12/1997 | Becker | 6,132,429 A | 10/2000 | Baker |
| 5,696,351 A | 12/1997 | Benn et al. | 6,142,992 A | 11/2000 | Cheng et al. |
| 5,696,441 A | 12/1997 | Mak et al. | 6,155,975 A | 12/2000 | Urich et al. |
| 5,702,386 A | 12/1997 | Stern et al. | 6,162,217 A | 12/2000 | Kannenberg et al. |
| 5,702,429 A | 12/1997 | King | 6,171,304 B1 | 1/2001 | Netherly et al. |
| 5,707,369 A | 1/1998 | Vaitekunas et al. | 6,188,211 B1 | 2/2001 | Rincon-Mora et al. |
| 5,712,772 A | 1/1998 | Telefus et al. | 6,203,541 B1 | 3/2001 | Keppel |
| 5,713,896 A | 2/1998 | Nardella | 6,210,403 B1 | 4/2001 | Klicek |
| 5,718,246 A | 2/1998 | Vona | 6,222,356 B1 | 4/2001 | Taghizadeh-Kaschani |
| 5,720,744 A | 2/1998 | Eggleston et al. | 6,228,080 B1 | 5/2001 | Gines |
| 5,722,975 A | 3/1998 | Edwards et al. | 6,228,081 B1 | 5/2001 | Goble |
| 5,729,448 A | 3/1998 | Haynie et al. | 6,231,569 B1 | 5/2001 | Bek |
| 5,733,281 A | 3/1998 | Nardella | 6,235,020 B1 | 5/2001 | Cheng et al. |
| 5,749,869 A | 5/1998 | Lindenmeier et al. | 6,238,387 B1 | 5/2001 | Miller, III |
| 5,749,871 A | 5/1998 | Hood et al. | 6,238,388 B1 | 5/2001 | Ellman |
| 5,755,715 A | 5/1998 | Stern | 6,241,725 B1 | 6/2001 | Cosman |
| 5,766,165 A | 6/1998 | Gentelia et al. | 6,245,065 B1 | 6/2001 | Panescu |
| 5,769,847 A | 6/1998 | Panescu | 6,246,912 B1 | 6/2001 | Sluijter et al. |
| 5,772,659 A | 6/1998 | Becker et al. | 6,251,106 B1 | 6/2001 | Becker et al. |
| 5,792,138 A | 8/1998 | Shipp | 6,258,085 B1 | 7/2001 | Eggleston |
| 5,797,802 A | 8/1998 | Nowak | 6,261,285 B1 | 7/2001 | Novak |
| 5,797,902 A | 8/1998 | Netherly | 6,261,286 B1 | 7/2001 | Goble et al. |
| 5,814,092 A | 9/1998 | King | 6,273,886 B1 | 8/2001 | Edwards |
| 5,817,093 A | 10/1998 | Williamson, IV et al. | 6,275,786 B1 | 8/2001 | Daners |
| 5,820,568 A | 10/1998 | Willis | 6,293,941 B1 | 9/2001 | Strul |
| 5,827,271 A | 10/1998 | Bussey et al. | 6,293,942 B1 | 9/2001 | Goble et al. |
| 5,830,212 A | 11/1998 | Cartmell | 6,296,636 B1 | 10/2001 | Cheng et al. |
| 5,836,909 A | 11/1998 | Cosmescu | 6,306,131 B1 | 10/2001 | Hareyama et al. |
| 5,836,943 A | 11/1998 | Miller, III | 6,306,134 B1 | 10/2001 | Goble et al. |
| 5,836,990 A | 11/1998 | Li | 6,309,386 B1 | 10/2001 | Bek |
| 5,846,236 A | 12/1998 | Lindenmeier et al. | 6,325,799 B1 | 12/2001 | Goble |
| 5,868,737 A | 2/1999 | Taylor et al. | 6,337,998 B1 | 1/2002 | Behl et al. |
| 5,868,739 A | 2/1999 | Lindenmeier et al. | 6,338,657 B1 | 1/2002 | Harper et al. |
| 5,868,740 A | 2/1999 | LeVeen et al. | 6,350,262 B1 | 2/2002 | Ashley |
| 5,871,481 A | 2/1999 | Kannenberg et al. | 6,358,245 B1 | 3/2002 | Edwards |
| 5,897,552 A | 4/1999 | Edwards et al. | 6,364,877 B1 | 4/2002 | Goble et al. |
| 5,908,444 A | 6/1999 | Azure | 6,383,183 B1 | 5/2002 | Sekino et al. |
| 5,913,882 A | 6/1999 | King | 6,391,024 B1 | 5/2002 | Sun et al. |
| 5,921,982 A | 7/1999 | Lesh et al. | 6,398,779 B1 * | 6/2002 | Buysse et al. ............ 606/34 |
| 5,925,070 A | 7/1999 | King et al. | 6,398,781 B1 | 6/2002 | Goble et al. |
| 5,931,836 A | 8/1999 | Hatta et al. | 6,402,741 B1 | 6/2002 | Keppel et al. |
| 5,938,690 A | 8/1999 | Law et al. | 6,402,743 B1 | 6/2002 | Orszulak et al. |
| 5,948,007 A | 9/1999 | Starkenbaum et al. | 6,416,509 B1 | 7/2002 | Goble et al. |
| 5,951,545 A | 9/1999 | Schilling | 6,436,096 B1 | 8/2002 | Hareyama |
| 5,951,546 A | 9/1999 | Lorentzen | 6,451,015 B1 | 9/2002 | Rittman, III et al. |
| 5,954,686 A | 9/1999 | Garito et al. | 6,458,121 B1 | 10/2002 | Rosenstock |
| 5,954,717 A | 9/1999 | Behl et al. | 6,464,689 B1 | 10/2002 | Qin |
| 5,954,719 A | 9/1999 | Chen et al. | 6,464,696 B1 | 10/2002 | Oyama |
| 5,961,344 A | 10/1999 | Rosales et al. | 6,498,466 B1 | 12/2002 | Edwards |
| 5,971,980 A | 10/1999 | Sherman | 6,506,189 B1 | 1/2003 | Rittman, III et al. |
| 5,976,128 A | 11/1999 | Schilling et al. | 6,508,815 B1 | 1/2003 | Strul |
| 5,983,141 A | 11/1999 | Sluijter et al. | 6,511,476 B2 | 1/2003 | Hareyama |

| Patent No. | Date | Inventor | Class |
|---|---|---|---|
| 6,511,478 B1 * | 1/2003 | Burnside et al. | 606/41 |
| 6,517,538 B1 | 2/2003 | Jacob et al. | |
| 6,524,308 B1 | 2/2003 | Muller et al. | |
| 6,547,786 B1 | 4/2003 | Goble | |
| 6,558,376 B2 | 5/2003 | Bishop | |
| 6,560,470 B1 | 5/2003 | Pologe | |
| 6,562,037 B2 | 5/2003 | Paton | |
| 6,565,559 B2 | 5/2003 | Eggleston | |
| 6,573,248 B2 | 6/2003 | Ramasamy et al. | |
| 6,575,969 B1 | 6/2003 | Rittman, III et al. | |
| 6,582,427 B1 | 6/2003 | Goble et al. | |
| 6,620,157 B1 | 9/2003 | Dabney et al. | |
| 6,623,423 B2 | 9/2003 | Sakurai et al. | |
| 6,629,973 B1 | 10/2003 | Wardell et al. | |
| 6,635,057 B2 | 10/2003 | Harano | |
| 6,645,198 B1 | 11/2003 | Bommannan et al. | |
| 6,648,883 B2 | 11/2003 | Francischelli | |
| 6,652,514 B2 | 11/2003 | Ellman | |
| 6,663,623 B1 | 12/2003 | Oyama et al. | |
| 6,663,624 B2 | 12/2003 | Edwards | |
| 6,666,860 B1 | 12/2003 | Takahashi | |
| 6,679,875 B2 | 1/2004 | Honda | |
| 6,682,527 B2 | 1/2004 | Strul | |
| 6,685,700 B2 | 2/2004 | Behl | |
| 6,685,701 B2 | 2/2004 | Orszulak et al. | |
| 6,685,703 B2 | 2/2004 | Pearson et al. | |
| 6,689,131 B2 | 2/2004 | McClurken | |
| 6,692,489 B1 | 2/2004 | Heim | |
| 6,693,782 B1 | 2/2004 | Lash | |
| 6,712,813 B2 | 3/2004 | Ellman | |
| 6,730,080 B2 | 5/2004 | Harano | |
| 6,733,495 B1 | 5/2004 | Bek | |
| 6,733,498 B2 | 5/2004 | Paton | |
| 6,740,079 B1 | 5/2004 | Eggers | |
| 6,740,085 B2 | 5/2004 | Hareyama | |
| 6,755,825 B2 | 6/2004 | Shoenman et al. | |
| 6,758,846 B2 | 7/2004 | Goble et al. | |
| 6,783,523 B2 | 8/2004 | Qin | |
| 6,786,905 B2 | 9/2004 | Swanson et al. | |
| 6,790,206 B2 | 9/2004 | Panescu | |
| 6,796,981 B2 * | 9/2004 | Wham et al. | 606/34 |
| 6,824,539 B2 | 11/2004 | Novak | |
| 6,830,569 B2 | 12/2004 | Thompson | |
| 6,843,789 B2 | 1/2005 | Goble | |
| 6,849,073 B2 | 2/2005 | Hoey | |
| 6,855,141 B2 | 2/2005 | Lovewell | |
| 6,855,142 B2 | 2/2005 | Harano | |
| 6,860,881 B2 | 3/2005 | Sturm | |
| 6,864,686 B2 | 3/2005 | Novak | |
| 6,875,210 B2 | 4/2005 | Refior | |
| 6,893,435 B2 | 5/2005 | Goble | |
| 6,923,804 B2 | 8/2005 | Eggers et al. | |
| 6,929,641 B2 | 8/2005 | Goble et al. | |
| 6,939,346 B2 | 9/2005 | Kannenberg et al. | |
| 6,939,347 B2 | 9/2005 | Thompson | |
| 6,942,660 B2 | 9/2005 | Pantera et al. | |
| 6,948,503 B2 | 9/2005 | Refior et al. | |
| 6,966,907 B2 | 11/2005 | Goble | |
| 6,989,010 B2 | 1/2006 | Francischelli et al. | |
| 6,994,704 B2 | 2/2006 | Qin et al. | |
| 6,994,707 B2 | 2/2006 | Ellman et al. | |
| 7,001,381 B2 | 2/2006 | Harano et al. | |
| 7,004,174 B2 | 2/2006 | Eggers et al. | |
| 7,041,096 B2 | 5/2006 | Malis et al. | |
| 7,044,948 B2 | 5/2006 | Keppel | |
| 7,044,949 B2 | 5/2006 | Orszulak et al. | |
| 7,060,063 B2 | 6/2006 | Marion et al. | |
| 7,062,331 B2 | 6/2006 | Zarinetchi et al. | |
| 7,063,692 B2 | 6/2006 | Sakurai et al. | |
| 7,066,933 B2 | 6/2006 | Hagg | |
| 7,122,031 B2 | 10/2006 | Edwards et al. | |
| 7,131,860 B2 | 11/2006 | Sartor et al. | |
| 7,137,980 B2 * | 11/2006 | Buysse et al. | 606/34 |
| 7,147,638 B2 | 12/2006 | Chapman et al. | |
| 7,160,293 B2 | 1/2007 | Sturm et al. | |
| 7,172,591 B2 | 2/2007 | Harano et al. | |
| 7,175,618 B2 | 2/2007 | Dabney et al. | |
| 7,175,621 B2 | 2/2007 | Heim et al. | |
| 7,211,081 B2 | 5/2007 | Goble | |
| 7,214,224 B2 | 5/2007 | Goble | |
| 7,220,260 B2 | 5/2007 | Fleming et al. | |
| 7,247,155 B2 | 7/2007 | Hoey et al. | |
| 7,250,746 B2 | 7/2007 | Oswald et al. | |
| 7,255,694 B2 | 8/2007 | Keppel | |
| 7,282,048 B2 | 10/2007 | Goble et al. | |
| 7,300,435 B2 * | 11/2007 | Wham et al. | 606/34 |
| 7,303,557 B2 | 12/2007 | Wham et al. | |
| 7,364,577 B2 | 4/2008 | Wham et al. | |
| 7,367,972 B2 | 5/2008 | Francischelli et al. | |
| RE40,388 E | 6/2008 | Gines | |
| 7,396,336 B2 | 7/2008 | Orszulak et al. | |
| 2001/0014804 A1 | 8/2001 | Goble et al. | |
| 2001/0029315 A1 | 10/2001 | Sakurai et al. | |
| 2001/0031962 A1 | 10/2001 | Eggleston | |
| 2002/0035363 A1 | 3/2002 | Edwards et al. | |
| 2002/0035364 A1 | 3/2002 | Schoenman et al. | |
| 2002/0052599 A1 | 5/2002 | Goble | |
| 2002/0068932 A1 | 6/2002 | Edwards | |
| 2002/0107517 A1 | 8/2002 | Witt et al. | |
| 2002/0111624 A1 | 8/2002 | Witt et al. | |
| 2002/0151889 A1 | 10/2002 | Swanson et al. | |
| 2002/0193787 A1 | 12/2002 | Qin | |
| 2003/0004510 A1 | 1/2003 | Wham et al. | |
| 2003/0060818 A1 | 3/2003 | Kannenberg | |
| 2003/0078572 A1 | 4/2003 | Pearson et al. | |
| 2003/0139741 A1 | 7/2003 | Goble et al. | |
| 2003/0153908 A1 | 8/2003 | Goble | |
| 2003/0163123 A1 | 8/2003 | Goble | |
| 2003/0163124 A1 | 8/2003 | Goble | |
| 2003/0171745 A1 | 9/2003 | Francischelli | |
| 2003/0181898 A1 | 9/2003 | Bowers | |
| 2003/0199863 A1 | 10/2003 | Swanson | |
| 2003/0225401 A1 | 12/2003 | Eggers et al. | |
| 2004/0002745 A1 | 1/2004 | Flemming | |
| 2004/0015159 A1 | 1/2004 | Slater et al. | |
| 2004/0015163 A1 | 1/2004 | Buysse et al. | |
| 2004/0015216 A1 | 1/2004 | DeSisto | |
| 2004/0019347 A1 | 1/2004 | Sakurai | |
| 2004/0024395 A1 | 2/2004 | Ellman | |
| 2004/0030328 A1 | 2/2004 | Eggers | |
| 2004/0030330 A1 | 2/2004 | Brassell et al. | |
| 2004/0044339 A1 | 3/2004 | Beller | |
| 2004/0049179 A1 | 3/2004 | Francischelli | |
| 2004/0054365 A1 | 3/2004 | Goble | |
| 2004/0059323 A1 | 3/2004 | Sturm et al. | |
| 2004/0068304 A1 | 4/2004 | Paton | |
| 2004/0082946 A1 | 4/2004 | Malis | |
| 2004/0095100 A1 | 5/2004 | Thompson | |
| 2004/0097912 A1 | 5/2004 | Gonnering | |
| 2004/0097914 A1 | 5/2004 | Pantera | |
| 2004/0097915 A1 | 5/2004 | Refior | |
| 2004/0116919 A1 | 6/2004 | Heim | |
| 2004/0133189 A1 | 7/2004 | Sakurai | |
| 2004/0138653 A1 | 7/2004 | Dabney et al. | |
| 2004/0138654 A1 | 7/2004 | Goble | |
| 2004/0143263 A1 | 7/2004 | Schechter et al. | |
| 2004/0147918 A1 | 7/2004 | Keppel | |
| 2004/0167508 A1 | 8/2004 | Wham et al. | |
| 2004/0172016 A1 * | 9/2004 | Bek et al. | 606/34 |
| 2004/0193148 A1 | 9/2004 | Wham et al. | |
| 2004/0230189 A1 | 11/2004 | Keppel | |
| 2004/0243120 A1 | 12/2004 | Orszulak et al. | |
| 2004/0260279 A1 * | 12/2004 | Goble et al. | 606/34 |
| 2005/0004564 A1 | 1/2005 | Wham | |
| 2005/0004569 A1 | 1/2005 | Witt et al. | |
| 2005/0021020 A1 | 1/2005 | Blaha et al. | |

| | | | | | | |
|---|---|---|---|---|---|---|
| 2005/0021022 | A1 | 1/2005 | Sturm et al. | EP | 836868 | 4/1998 |
| 2005/0101949 | A1 | 5/2005 | Harano et al. | EP | 878169 | 11/1998 |
| 2005/0101951 | A1 | 5/2005 | Wham | EP | 1051948 | 11/2000 |
| 2005/0113818 | A1 | 5/2005 | Sartor | EP | 1053720 | 11/2000 |
| 2005/0113819 | A1 | 5/2005 | Wham | EP | 1151725 | 11/2001 |
| 2005/0149151 | A1 | 7/2005 | Orszulak | EP | 1293171 | 3/2003 |
| 2005/0182398 | A1 | 8/2005 | Paterson | EP | 1472984 | 11/2004 |
| 2005/0197659 | A1 | 9/2005 | Bahney | EP | 1495712 | 1/2005 |
| 2005/0203504 | A1 | 9/2005 | Wham et al. | EP | 1500378 | 1/2005 |
| 2006/0025760 | A1 | 2/2006 | Podhajsky | EP | 1535581 | 6/2005 |
| 2006/0079871 | A1 | 4/2006 | Plaven et al. | EP | 1609430 | 12/2005 |
| 2006/0161148 | A1 | 7/2006 | Behnke | EP | 1645235 | 4/2006 |
| 2006/0178664 | A1 | 8/2006 | Keppel | EP | 0880220 B1 | 6/2006 |
| 2006/0224152 | A1 | 10/2006 | Behnke et al. | EP | 1707143 | 10/2006 |
| 2006/0281360 | A1 | 12/2006 | Sartor et al. | EP | 1810628 | 7/2007 |
| 2007/0038209 | A1 | 2/2007 | Buysse et al. | EP | 1810630 | 7/2007 |
| 2007/0093800 | A1 | 4/2007 | Wham et al. | EP | 1810633 | 7/2007 |
| 2007/0093801 | A1 | 4/2007 | Behnke | FR | 1275415 | 10/1961 |
| 2007/0135812 | A1 | 6/2007 | Sartor | FR | 1347865 | 11/1963 |
| 2007/0173802 | A1 | 7/2007 | Keppel | FR | 2313708 | 12/1976 |
| 2007/0173803 | A1 | 7/2007 | Wham et al. | FR | 2502935 | 10/1982 |
| 2007/0173804 | A1 | 7/2007 | Wham et al. | FR | 2517953 | 6/1983 |
| 2007/0173805 | A1 | 7/2007 | Weinberg et al. | FR | 2573301 | 5/1986 |
| 2007/0173806 | A1 | 7/2007 | Orszulak et al. | GB | 607850 | 8/1948 |
| 2007/0173810 | A1 | 7/2007 | Orszulak | GB | 855459 | 11/1960 |
| 2007/0173813 | A1 | 7/2007 | Odom | GB | 902775 | 8/1962 |
| 2007/0208339 | A1 | 9/2007 | Arts et al. | GB | 2164473 | 3/1986 |
| 2007/0225698 | A1 | 9/2007 | Orszulak et al. | GB | 2214430 | 9/1989 |
| 2007/0250052 | A1 | 10/2007 | Wham | GB | 2358934 A | 8/2001 |
| 2007/0265142 | A1 | 11/2007 | Behnke et al. | SU | 166452 | 1/1965 |
| 2007/0282320 | A1 | 12/2007 | Buysse et al. | SU | 727201 | 4/1980 |
| 2008/0015564 | A1 | 1/2008 | Wham et al. | WO | WO92/06642 | 4/1992 |
| 2008/0039831 | A1 | 2/2008 | Odom et al. | WO | WO93/24066 | 12/1993 |
| 2008/0039836 | A1 | 2/2008 | Odom et al. | WO | WO94/24949 | 11/1994 |
| 2008/0082094 | A1 | 4/2008 | McPherson et al. | WO | WO94/28809 | 12/1994 |
| 2008/0125767 | A1 | 5/2008 | Blaha | WO | WO95/09577 | 4/1995 |
| | | | | WO | WO95/19148 | 7/1995 |
| | | FOREIGN PATENT DOCUMENTS | | WO | WO96/02180 | 2/1996 |
| | | | | WO | WO96/04860 | 2/1996 |
| DE | | 1099658 | 2/1961 | WO | WO96/08794 | 3/1996 |
| DE | | 1139927 | 11/1962 | WO | WO96/18349 | 6/1996 |
| DE | | 1149832 | 6/1963 | WO | WO96/29946 | 10/1996 |
| DE | | 1439302 | 1/1969 | WO | WO96/39086 | 12/1996 |
| DE | | 2439587 | 2/1975 | WO | WO96/39914 | 12/1996 |
| DE | | 2455174 | 5/1975 | WO | WO 9639086 A1 * | 12/1996 |
| DE | | 2407559 | 8/1975 | WO | WO97/06739 | 2/1997 |
| DE | | 2602517 | 7/1976 | WO | WO97/06740 | 2/1997 |
| DE | | 2504280 | 8/1976 | WO | WO97/06855 | 2/1997 |
| DE | | 2540968 | 3/1977 | WO | WO97/11648 | 4/1997 |
| DE | | 2820908 | 11/1978 | WO | WO97/17029 | 5/1997 |
| DE | | 2803275 | 8/1979 | WO | WO02/11634 | 2/2002 |
| DE | | 2823291 | 11/1979 | WO | WO02/45589 | 6/2002 |
| DE | | 2946728 | 5/1981 | WO | WO02/47565 | 6/2002 |
| DE | | 3143421 | 5/1982 | WO | WO02/053048 | 7/2002 |
| DE | | 3045996 | 7/1982 | WO | WO02/088128 | 7/2002 |
| DE | | 3120102 | 12/1982 | WO | WO03/090630 | 11/2003 |
| DE | | 3510586 | 10/1986 | WO | WO03/090635 | 11/2003 |
| DE | | 3604823 | 8/1987 | WO | WO03/092520 | 11/2003 |
| DE | | 390937 | 4/1989 | WO | WO2004/028385 | 4/2004 |
| DE | | 3904558 | 8/1990 | WO | WO2004/098385 | 4/2004 |
| DE | | 3942998 | 7/1991 | WO | WO2004/103156 | 12/2004 |
| DE | | 4339049 A1 | 5/1995 | WO | WO2005/046496 | 5/2005 |
| DE | | 19717411 | 11/1998 | WO | WO2005/048809 | 6/2005 |
| DE | | 19848540 A1 | 5/2000 | WO | WO2005/050151 | 6/2005 |
| EP | | 246350 | 11/1987 | WO | WO2005048809 A1 | 6/2005 |
| EP | | 310431 | 4/1989 | WO | WO2005/060365 | 7/2005 |
| EP | | 325456 | 7/1989 | WO | WO2005/060849 | 7/2005 |
| EP | | 336742 | 10/1989 | | | |
| EP | | 390937 | 10/1990 | | | |
| EP | | 556705 | 8/1993 | | | |
| EP | | 0569130 A1 | 11/1993 | | | |
| EP | | 608609 | 8/1994 | | | |
| EP | | 0694291 | 1/1996 | | | |

OTHER PUBLICATIONS

International Search Report EP 07010673.7 dated Sep. 24, 2007.
International Search Report EP 06000708.5 dated Apr. 21, 2006.

International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . . " Journal of Applied Sciences-Yingyong Kexue Xuebao, Shanghai CN, vol. 23 No. 2;(Mar. 2005); 160-164.
Alexander et al., "Magnetic Resonance Image-Directed Stereotactic Neurosurgery: Use of Image Fusion with Computerized Tomography to Enhance Spatial Accuracy" Journal Neurosurgery, 83: (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984). pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedance" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation-'COA-COMP'" Neurosurgical Review 7:2-3 (1984) pp. 187-190.
Wald et al., "Accidental Burns" JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
Bergdahl et al. "Studies on Coagulation and the Development of an Automatic Computerized Bipolar Coagulator" J.Neurosurg, vol. 75, Jul. 1991, pp. 148-151.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.

* cited by examiner

METHOD AND SYSTEM FOR PROGRAMMING AND CONTROLLING AN ELECTROSURGICAL GENERATOR SYSTEM

PRIORITY

This application claims priority to an application entitled "METHOD AND SYSTEM FOR PROGRAMMING AND CONTROLLING AN ELECTROSURGICAL GENERATOR SYSTEM" filed in the United States Patent and Trademark Office on May 1, 2003 and assigned Ser. No. 60/466,954, the contents of which are hereby incorporated by reference.

BACKGROUND

1. Technical Field

The present disclosure is directed to electrosurgery and, in particular, to a method and system for programming and controlling an electrosurgical generator system.

2. Description of the Related Art

Electrosurgery entails the use of electrosurgical energy to cut or coagulate tissue, or perform some other type of surgical procedure. An electrosurgical generator system is used for generating the electrosurgical energy and delivering the same to an electrode connected to the generator. The electrode is then brought into contact with tissue and depending on the frequency and other parameters of the electrosurgical energy, the tissue is either cut, coagulated, sealed, etc.

In order to achieve desired surgical results when operating the electrosurgical generator system in one of several control modes, e.g., cut, coagulate and blend, the electrosurgical generator system needs to be programmed to generate electrosurgical energy having output parameters with predetermined values. These desired output parameters typically include the frequency, power (amplitude), duty cycle, and waveform-type of the electrosurgical energy, as well as the output current and output voltage of the electrosurgical generator system.

It is evident that by programming the electrosurgical generator system, one can control various parameters, including other factors, such as the maximum allowable temperature of the tissue during electrosurgery, rate of change of impedance, etc., prior to initiating the electrosurgical procedure.

Accordingly, the present disclosure provides a method and system capable of enabling an individual to quickly create new electrosurgical applications without major re-programming of the software system of an electrosurgical generator system.

SUMMARY

A method and system are disclosed capable of enabling an individual to quickly create new electrosurgical applications without major re-programming of the software system of an electrosurgical generator system. In one embodiment, the method and system of the present disclosure enables an individual to efficiently create new application modes by creating configuration or command files for downloading or programming these new modes into the electrosurgical generator system for creating new surgical applications without changing the underlying software system.

A control loop system is chiefly responsible for the operation of the electrosurgical generator system and it is composed of three basic components: an inner loop system which is responsible for changing and sculpting basic RF output; an outer loop system which is responsible for setting the output target of the inner loop based on a variety of algorithms such as the control of temperature; and a configuration control system which is responsible for reprogramming the inner and outer loop systems "on-the-fly" or in virtual real-time for the inner and outer loop systems to change operation.

All user programming is preferably accomplished using at least one input device, such as a keyboard, touch-screen display, etc., while the software programming may be based on a file-based programming language to input programming commands to the electrosurgical generator system. The combination of the two inputted programming commands are stored into command files and define all aspects and parameters of the electrosurgical generator system.

The simple input and storage of the programming commands according to the present disclosure allows for easy creation and modification of new electrosurgical generator modes. For example, a mode can be created by inputting programming commands and storing the same in a command file, subsequent modes can easily be created by modifying associated parameters and storing them as a new command file.

Further features of the above embodiments will become more readily apparent to those skilled in the art from the following detailed description when taken in conjunction with the drawings.

BRIEF DESCRIPTION OF THE DRAWINGS

Various embodiments will be described herein below with reference to the drawings wherein.

DETAILED DESCRIPTION OF PREFERRED EMBODIMENTS

Figure 1:
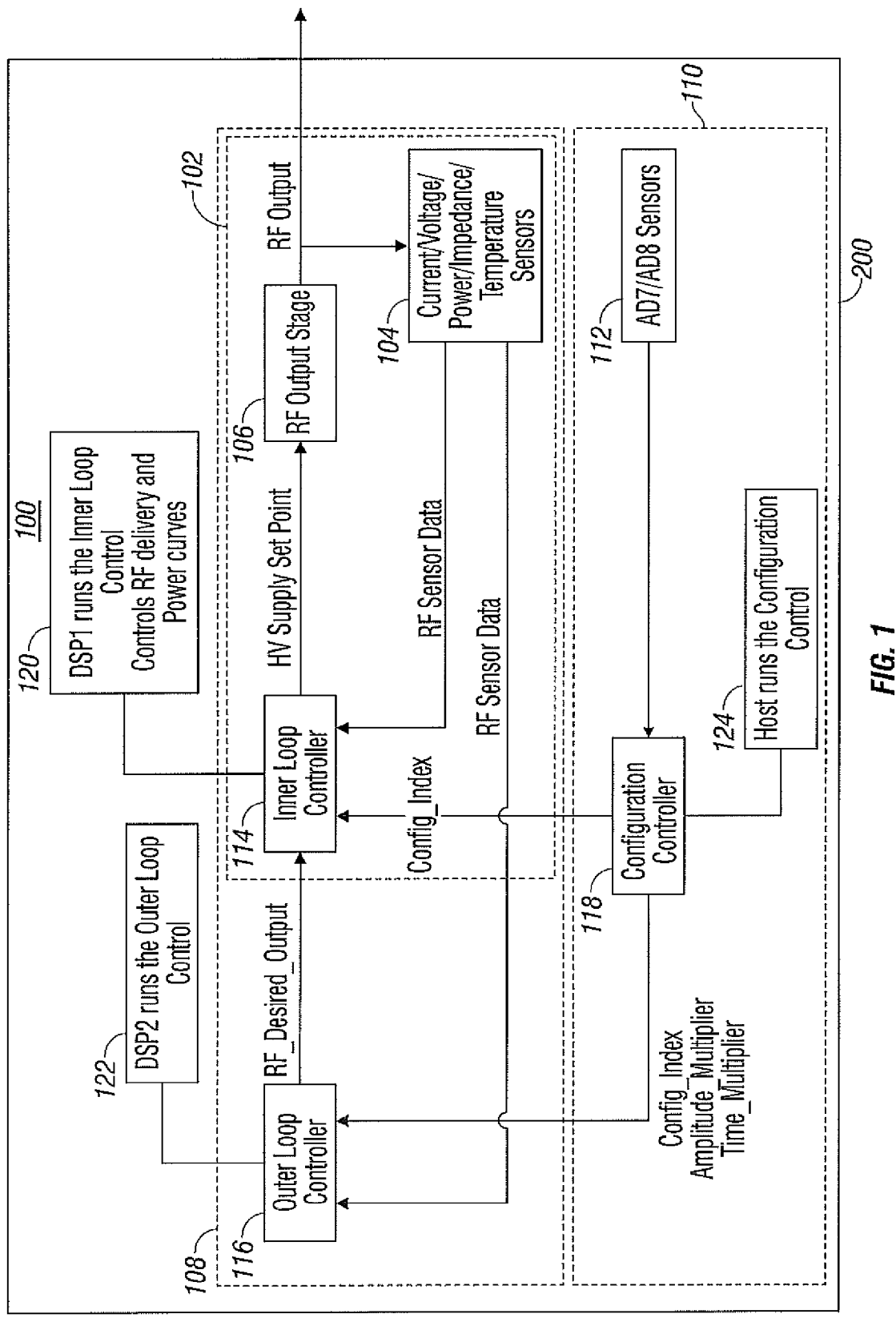
FIG. 1 is a block diagram of a control loop system of an electrosurgical generator system in accordance with the present disclosure.

Reference should be made to the drawings where like reference numerals refer to similar elements. Referring to FIG. 1, there is shown a block diagram of an embodiment of a control loop system for an electrosurgical generator system in accordance with the present disclosure. The control loop system is designated generally by reference numeral 100 and it is designed to enable a software developer to efficiently program and control the operation of the electrosurgical generator system 200. The electrosurgical generator system 200 is particularly designed for the easy creation of multiple different electrosurgical systems. The method and system of the present disclosure enables an individual to efficiently create new application modes by creating configuration or command files for downloading or programming these new modes into the electrosurgical generator system for creating new surgical applications without changing the underlying software system.

The control loop system 100 is chiefly responsible for the operation of the electrosurgical generator system 200 and it is composed of three basic components: an inner loop system 102 which is responsible for changing and sculpting basic RF output (e.g., current, power, or voltage output, duty cycle, frequency), and inner loop control system dynamics of an RF output stage 106 based on user and/or sensor inputs from various sensors 104 and/or user input devices (not shown); an outer loop system 108 which is responsible for controlling the inner loop setpoint based on a variety of algorithms (e.g., temperature control, impedance control, pulse control, vessel sealing, etc.) based on user and/or sensor inputs from the various sensors 104 and time and/or user input devices (not shown); and a configuration control system 110 which is responsible for changing the programming of the inner and outer loop systems 102, 108 "on-the-fly" or in virtual real-time based on user or sensor inputs received from various sensors 112 and/or user input devices (not shown).

Figure 2A:
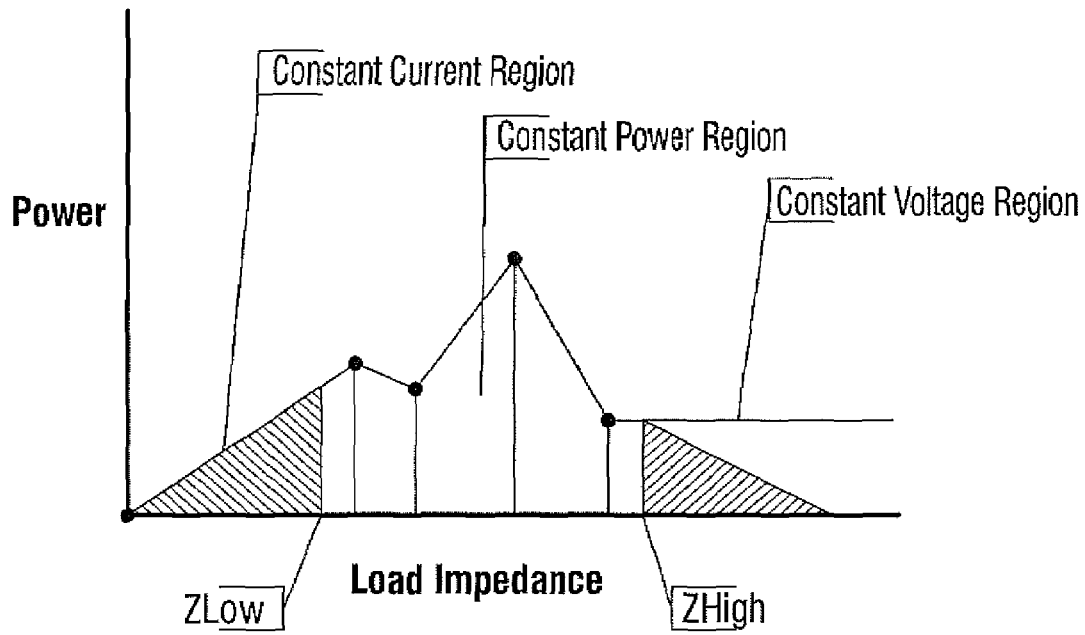
FIGS. 2A-D illustrate charts showing output waveforms indicative of various output parameters of the electrosurgical generator system in accordance with the present disclosure.

FIGS. 2A-2D illustrate charts showing the RF output indicative of various inner loop output parameters of the electrosurgical generator system 200. FIG. 2A is a chart plotting the output power versus the load impedance where the output power is sculpted, e.g., the output power is not constant over a load impedance range. The electrosurgical generator system 200 is able to control the inner loop system 102 to sculpt the output power based on user and/or sensor inputs received from various sensors 104, 112 and/or user input devices.

Figure 2B:
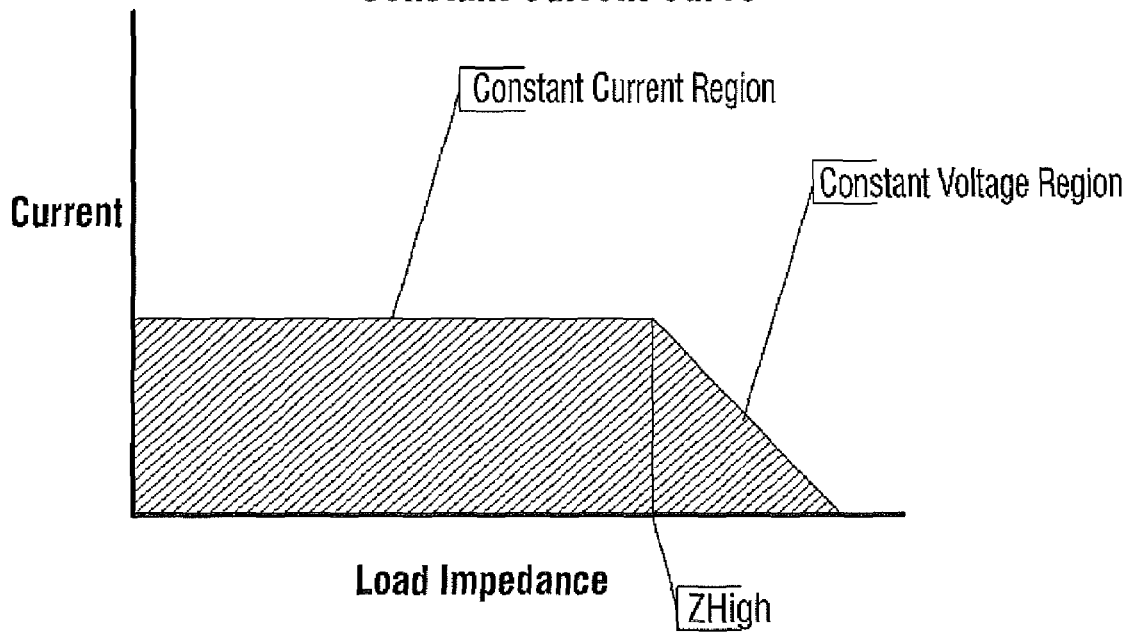
Figure 2C:
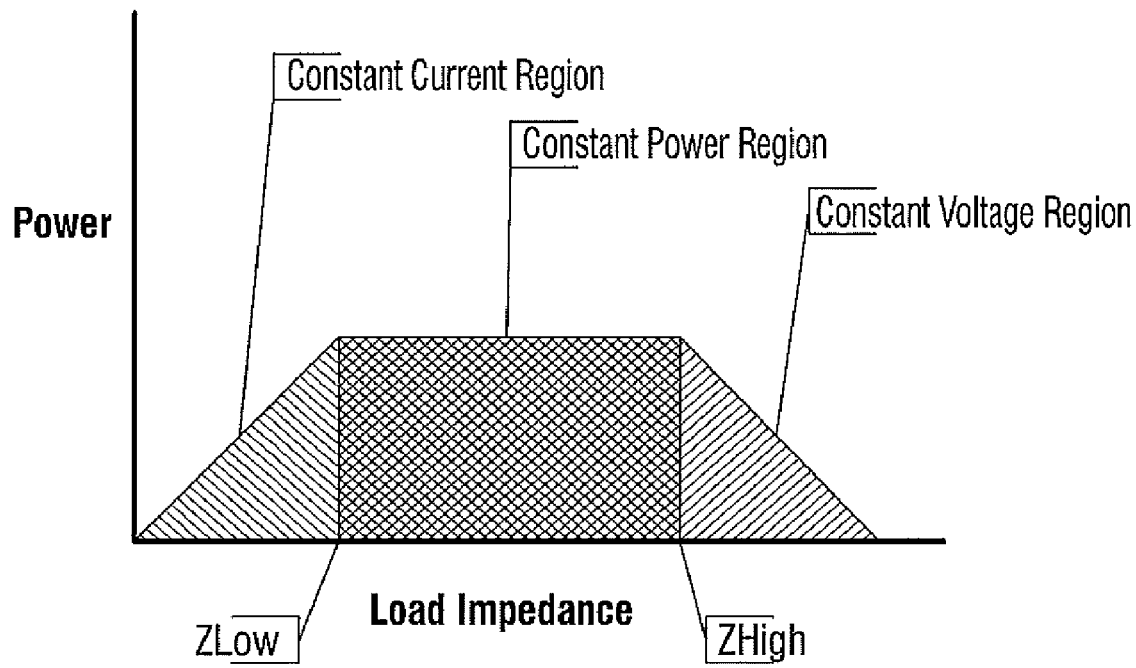
Figure 2D:
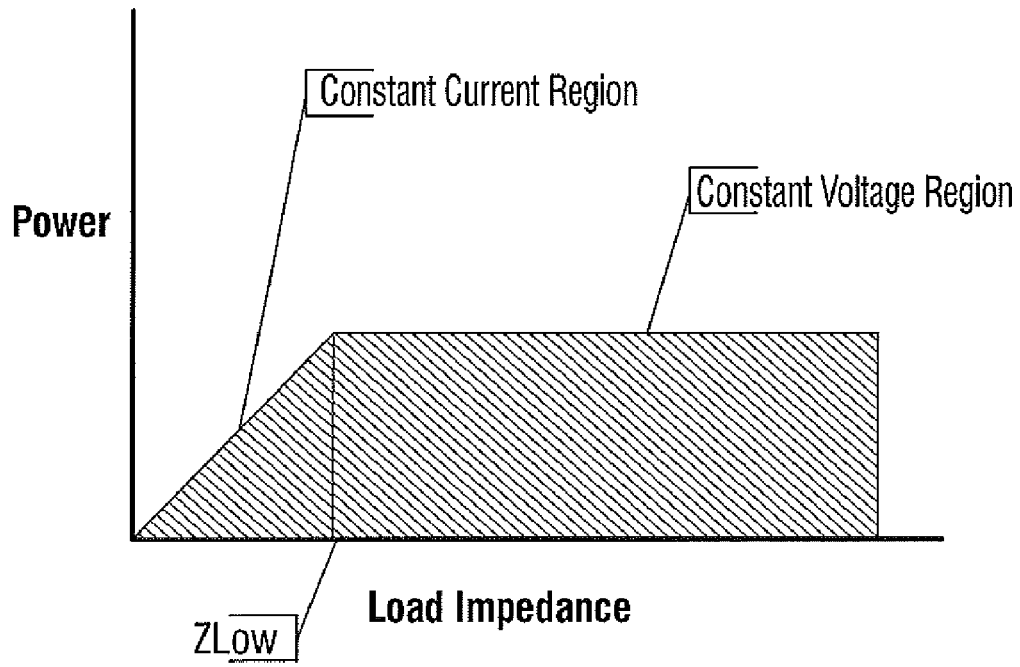

With reference to FIGS. 2B-2D, the electrosurgical generator system 200 is also able to maintain the output constant. FIG. 2B shows the output current being maintained at a constant level over a load impedance range. FIG. 2C shows the output power being maintained at a constant level over a load impedance range. FIG. 2D shows the output voltage being maintained at a constant level over a load impedance range.

As shown by FIG. 1, the inner loop system 102 is controlled by an inner loop controller 114, the outer loop system 108 is controlled by an outer loop controller 116, and the configuration control system 110 is controlled by a configuration controller 118. The controllers 114, 116 perform their various functions by the execution of a set of programmable instructions by at least one microprocessor and/or at least one digital signal processor (DSP), e.g., DSPs 120, 122, respectively.

The configuration controller 118 performs its various functions by the execution of a set of programmable instructions executed by at least one microprocessor and/or a DSP, e.g., DSP 124. The controllers 114, 116, 118 are configured for receiving inputted programming commands for operating the electrosurgical generator system 200.

All programming is preferably accomplished using at least one input device, such as a keyboard, touch-screen display, remote computer system, etc., to input the programming commands to the electrosurgical generator system 200. The inputted programming commands are stored into command files within at least one memory module, such as a RAM module, and define all aspects and parameters of the electrosurgical generator system 200.

The simple input or download and storage of the programming commands according to the present disclosure allows for easy creation and modification of new electrosurgical generator modes. For example, one mode can be created by inputting programming commands and storing the same in a command file. A new mode can be created based on the original programming.

A description will now be presented with reference to programming the at least one microprocessor by way of a programming language in a preferred embodiment for controlling and programming the electrosurgical generator system 200 of the present disclosure.

I. Configuration Control System

The set of programmable instructions for operating the electrosurgical generator system 200 in accordance with the present disclosure has been designed to enable two analog inputs to the configuration controller 118 to control the mode (outer and inner loop programming) and the desired output (current (I), power (P), voltage (V), etc. depending on the control mode selected) of the electrosurgical generator system 200.

In an exemplary embodiment of the present disclosure, the method of mode control is accomplished by making a data structure, e.g., Local_Cfg[ ], an array. When a mode switch is desired, a host variable, e.g., Config_Index, is adjusted and then copied to a processing file, e.g., Out_Local_IO.Config_Index, where it switches an active command file, e.g., Local_Cfg[Local_IO.Config_Index].

The method of desired output programming is accomplished by adjusting a host variable, e.g., Out_Local_IO.Desired_Amplitude_Multiplier, where Desired_Amplitude_Multiplier represents a multiplier value for adjusting the output curves of the outer loop system 108 when enabled or is passed directly to the inner loop system 102 as a current/power/voltage level if the outer loop system 108 is disabled.

I.a. Configuration Selection Control

The configuration selection is programmed by filling the variable, e.g., Local_Cfg[ ], with the data from the sets of command files. The configuration index is first specified, then the data is read from the command files, then the next index is specified, etc.

I.a.1. Command File Programming

The programming of the configuration control system 110 is controlled by a Meta command file. This command file loads the Local_Cfg[ ] array with each configuration and specifies how the configuration and Desired_Amplitude_Multiplier is controlled.

To specify which location in the Local_Cfg[ ] array is to be filled, the following command is used:

CONFIG_INDEX x, where x specifies the location to be filled (0-7).

To specify which configuration is to be loaded in the memory module, the following command is used:

INCLUDE_FILE xxx, where xxx is a valid path and filename of outer and inner loop command files which define the configuration to be loaded in the memory module.

An example is provided below:

```
// Load Config Index Location 0
#CONFIG_INDEX        0
// Inner Loop definition
#INCLUDE_FILE
C:\LRT_TRT\Code\Cmd_Files\CP_472k_Inner_Loop.cmd
// Load Outer Loop definition
#INCLUDE_FILE
C:\LRT_TRT\Code\Cmd_Files\Temp_Outer_Loop.cmd
// Load Config Index location 1
#CONFIG_INDEX        1
// Inner Loop definition
#INCLUDE_FILE
C:\LRT_TRT\Code\Cmd_Files\CP_250k_Inner_Loop.cmd
// Load Outer Loop definition
#INCLUDE_FILE
C:\LRT_TRT\Code\Cmd_Files\DZ_Outer_Loop.cmd
```

I.b. Mode Selection Control

Mode selection can be programmed to be selected by one of three inputs: a user input device (e.g., a keyboard), AD7 or AD8, where AD7 and AD8 are sensor modules. Mode modification can be programmed to be controlled by one of three inputs: a user input device (e.g., a keyboard), AD7 or AD8. The operation of the mode selection and mode modification control is that one control input can be set to select the mode, then another control can make the fine adjustments to that selection. The mode modification may be done in an additive fashion as shown in the example below:

Actual Mode=Mode(*AD*7)+Modifier(*AD*8).

I.b.1. Command File Programming

A Mode Selection Algorithm which controls how the active mode switching is set may be selected.

The valid exemplary selection choices are the following:

```
#MODE_SEL_ALG_IS_KEYBOARD -keyboard sets the active mode.
#MODE_SEL_ALG_IS_AD7
#MODE_SEL_ALG_IS_AD8
```

A Mode Modification Algorithm which controls how the active mode switching is set by a modifier also may be selected.

The valid exemplary selection choices are the following:

```
#MODE_MODIFIER_SEL_IS_OFF -No modifier is used on active mode switching.
#MODE_MODIFIER_SEL_IS_AD7
#MODE_MODIFIER_SEL_IS_AD8
```

I.c. Amplitude Selection Control

Amplitude multiplication selection can be selected by one of three inputs: a user input device (e.g., a keyboard), AD7 or AD8. Amplitude multiplication modification can be controlled by one of three inputs: keyboard, AD7 or AD8. The operation of the selection and modification control is that one control input can be set to select the amplitude multiplication, then another control can make fine adjustments to that selection. The amplitude multiplication modification may be done in an additive fashion as shown in the example below:

Actual Amp=Amp(*AD*7)+Modifier(*AD*8).

It is noted that amplitude multiplication is used both for outer loop programming and if the outer loop system 108 is off, for the desired output of the inner loop system 102. When the outer loop system 108 is on, a normalized curve is designed which specifies the desired output over time, and an amplitude multiplier controls the amplitude of this curve. A time multiplier controls the time scale at which this curve is interpreted.

I.c.1. Command File Programming

The Output Amplitude Multiplier Algorithm controls how an output amplitude multiplier is set.

The valid exemplary selection choices are the following:

```
#AMP_SEL_ALG_IS_KEYBOARD
#AMP_SEL_ALG_IS_AD7
#AMP_SEL_ALG_IS_AD8
```

The Output Amplitude Modifier Algorithm controls how an output amplitude modifier is set.

The valid selection exemplary choices are the following:

```
#AMP_MODIFIER_SEL_IS_OFF
#AMP_MODIFIER_SEL_IS_AD7
#AMP_MODIFIER_SEL_IS_AD8
```

I.d. RF Activation Control

The control loop system 100 can be programmed to activate RF output based on either AD7 or AD8 inputs. A user input device, such as footswitch of the electrosurgical generator system 200 can also be used to activate RF output. The threshold of activation can be programmed.

I.d.1. Command File Programming

RF Activation Programming selects which source will start the RF activation:

```
#RF_ACT_IS_FOOTSWITCH -Normal footswitch activation.
#RF_ACT_IS_AD7 -Activated by AD7 voltage above threshold.
#RF_ACT_IS_AD8 -Activated by AD8 voltage above threshold.
#RF_ACT_VOLTAGE_THRESHOLD -Specifies the voltage threshold
```

It is noted that in a preferred embodiment, footswitch activation of the electrosurgical generator system 200 is always active, even if inputs AD7 or AD8 are selected.

I.e. AD7/AD8 Curves

The programming of sensor input controls is accomplished through the creation of a "map" which specifies the amplitude multiplier and configuration index and maps these values to an input voltage.

I.e.1. Command File Programming

The Mode Control and Amplitude Multiplier Control Maps for each Control Voltage (AD7/AD8) need to be specified.

An exemplary table is shown:

| Sensor Voltage | Amplitude Multiplier | Configuration Index |
| --- | --- | --- |
| 1.0 | 0.9 | 1 |
| 2.0 | 1.1 | 2 |

Exemplary valid programming commands are:

```
#AD7_MAP_V_x  y
#AD7_MAP_AMP_xy
#AD7_MAP_INDEX_x       y
#AD8_MAP_V_x  y
#AD8_MAP_AMP_xy
#AD8_MAP_INDEX_x       y
where x = 0 - 7
where y is the programmed value
```

Example for AD8:

| | | |
| --- | --- | --- |
| #AD8_MAP_V_0 | 1.47 | |
| #AD8_MAP_AMP_0 | 0.0 | |
| #AD8_MAP_INDEX_0 | | 0 |
| #AD8_MAP_V_1 | 1.57 | |
| #AD8_MAP_AMP_1 | 0.0 | |
| #AD8_MAP_INDEX_1 | | 0 |
| #AD8_MAP_V_2 | 1.66 | |

-continued

| | | |
|---|---|---|
| #AD8_MAP_AMP_2 | 0.0 | |
| #AD8_MAP_INDEX_2 | | 0 |
| #AD8_MAP_V_3 | 1.76 | |
| #AD8_MAP_AMP_3 | 0.0 | |
| #AD8_MAP_INDEX_3 | | 0 |
| #AD8_MAP_V_4 | 1.85 | |
| #AD8_MAP_AMP_4 | 0.0 | |
| #AD8_MAP_INDEX_4 | | 0 |
| #AD8_MAP_V_5 | 1.94 | |
| #AD8_MAP_AMP_5 | 0.0 | |
| #AD8_MAP_INDEX_5 | | 0 |
| #AD8_MAP_V_6 | 2.04 | |
| #AD8_MAP_AMP_6 | 0.0 | |
| #AD8_MAP_INDEX_6 | | 0 |
| #AD8_MAP_V_7 | 6.00 | |
| #AD8_MAP_AMP_7 | 0.0 | |
| #AD8_MAP_INDEX_7 | | 0 |

I.e.2. Related Routines

| | |
|---|---|
| 894 HOST.CPP | 37 \|--Process_Sensor_Control |
| \| \| | |
| 1313 HOST.CPP | 38 \| \|--Get_AD7_Sensor_Map_Index |
| \| \| | |
| 1343 HOST.CPP | 39 \| \|--Get_AD8_Sensor_Map_Index |
| \| \| | |
| 1427 HOST.CPP | 40 \| \|--Update_Sensor_Pads |
| 41 \| \| \|..sqrt | |
| \| \| | |
| 709 HOST_I~1.CPP | 42 \| \|--Send_TCL_Data |
| 926 HOST_I~1.CPP | 43 \| \| \|--Delay {11} |
| 44 \| \| \|..SET_DATA_IN | |
| \| \| | |
| 646 HOST_I~1.CPP | 45 \| \|--Get_Keying_Request |
| 46 \| \| \|..DIG_In_Prt | |
| \| \| | |
| | 47 \| \|..AI_VRead printf |

II. Outer Loop System

The outer loop system 108 is responsible for controlling the setpoint (e.g. DSP_Shared_Data.RF_Desired_Output) for the inner loop system 102. The concept of temperature control will be used to describe how this is accomplished, however other control methods may be used, such as but not limited to rate of change of temperature control, impedance control and rate of change of impedance control. In temperature control mode, the outer loop system 108 is programmed to follow a specific temperature vs. time curve. The outer loop system 108 uses the temperature versus time curve to retrieve its target temperature after lapse of a specified time, e.g., after a procedure has started. If the temperature is low, then the outer loop system 108 raises the inner loop setpoint. If the temperature is high, then the outer loop system 108 lowers the inner loop setpoint. The inner loop system 102 then attempts to deliver RF as specified by the inner loop setpoint, and thus raise or lower the temperature.

The user is given control of the amplitude multiplier and/or the time multiplier which adjust the temperature versus time curves. The curves are specified as normalized values from 0.0 to 1.0. Thus, the temperature curve can be increased by increasing the amplitude multiplier:

Target Temperature=Temperature_Curve(Time)*Amplitude Multiplier;

The time scale in which the curve is executed may also be adjusted by modifying the time multiplier in a similar fashion to the target temperature, thus:

Time=Time Curve*Time Multiplier;

The outer loop system 108 operates in selectable modes for controlling temperature, rate of change of impedance and work (in Joules). The source code enables the addition of other modes, if desired.

The outer loop system 108 can also be turned off. In this case, the amplitude multiplier is passed directly to the inner loop system 102 as the setpoint and the time multiplier is not used.

Sitting on top of all the outer loop modes and algorithms is a pulsing control system. This pulsing control system allows the user to specify pulsing waveform pattern parameters, such as the number of pulses in a burst of pulses, the duty cycle (e.g., ratio of on time to off time), delay time (e.g., time between bursts of pulses), frequency (e.g., 1/time between rising edges of 'on time'), and on/off amplitude envelope (e.g., amplitude pattern of a burst of pulses) for pulses to be delivered.

II.a. Command File Programming

Outer loop Proportional Integral Derivative (PID) parameters control the dynamic behavior of the outer loop system 108. Preferably, the control system is a PID system.

| | |
|---|---|
| #OUTER_LOOP_P | 1.0 |
| #OUTER_LOOP_I | 0.0001 |
| #OUTER_LOOP_D | 0.0 |

Outer loop control output limit parameters, including minimum and maximum inner loop target values, are used to limit the range that the outer loop system 108 can change the inner loop setpoint. The outer loop control output limit parameters are sent from the outer loop system 108 to the inner loop system 102. The data is either in watts, amps or volts depending on the inner loop programming (e.g., using curves selected from I, P, V curves).

Exemplary limits are:

| |
|---|
| #OUTER_LOOP_OUTPUT_MAX 150.0 |
| #OUTER_LOOP_OUTPUT_MIN 0.0 |

An outer loop start point is the starting inner loop target. This gives the outer loop system 108 a point at which to start prior to starting active control.

An exemplary start point is:
OUTER_LOOP_OUTPUT_START 5.0

Outer loop curve types specify which outer loop algorithm is to be executed. The software system may support numerous different algorithms. A few exemplary valid types are shown below:

Valid types are:

| |
|---|
| #OUTER_LOOP_ALG_IS_TEMPERATURE |
| #OUTER_LOOP_ALG_IS_OFF |

An outer loop amplitude curve specifies the target amplitude part of the target versus time curve that the outer loop system 108 uses to determine its target.

A corresponding table is provided which specifies the shape of the amplitude curve. The target value=OUTER_LOOP_CURVE_AMP [TIME*TIME_Multiplier]*AMPLITUDE_Multiplier
OUTER_LOOP_CURVE_AMP_03 0.01
Exemplary Amplitude Curve:

| | |
|---|---|
| #OUTER_LOOP_CURVE_AMP_00 | 0.2 |
| #OUTER_LOOP_CURVE_AMP_01 | 0.4 |
| #OUTER_LOOP_CURVE_AMP_02 | 0.6 |
| #OUTER_LOOP_CURVE_AMP_03 | 0.8 |
| #OUTER_LOOP_CURVE_AMP_04 | 1.0 |
| #OUTER_LOOP_CURVE_AMP_05 | 1.0 |
| #OUTER_LOOP_CURVE_AMP_06 | 1.0 |
| #OUTER_LOOP_CURVE_AMP_07 | 1.0 |
| #OUTER_LOOP_CURVE_AMP_08 | 1.0 |
| #OUTER_LOOP_CURVE_AMP_09 | 1.0 |
| #OUTER_LOOP_CURVE_AMP_10 | 1.0 |
| #OUTER_LOOP_CURVE_AMP_11 | 1.0 |
| #OUTER_LOOP_CURVE_AMP_12 | 1.0 |
| #OUTER_LOOP_CURVE_AMP_13 | 1.0 |
| #OUTER_LOOP_CURVE_AMP_14 | 1.0 |
| #OUTER_LOOP_CURVE_AMP_15 | 1.0 |
| #OUTER_LOOP_CURVE_AMP_16 | 1.0 |
| #OUTER_LOOP_CURVE_AMP_17 | 1.0 |
| #OUTER_LOOP_CURVE_AMP_18 | 1.0 |
| #OUTER_LOOP_CURVE_AMP_19 | 1.0 |
| #OUTER_LOOP_CURVE_AMP_20 | 1.0 |
| #OUTER_LOOP_CURVE_AMP_21 | 1.0 |
| #OUTER_LOOP_CURVE_AMP_22 | 1.0 |
| #OUTER_LOOP_CURVE_AMP_23 | 1.0 |
| #OUTER_LOOP_CURVE_AMP_24 | 1.0 |

Outer loop time curve parameters specify the shape of the time curve, where each location in the OUTER_LOOP_CURVE_AMP [ ] corresponds to the values in the time curve. The time multiplier thus allows the user to expand or contract the time at which the AMP curve generates the targets to the outer loop.

It is noted that the location may be specified with two digits, for example:
OUTER_LOOP_CURVE_TIME_03 0.01
Exemplary Time Curve:

| | |
|---|---|
| #OUTER_LOOP_CURVE_TIME_00 | 0.0 |
| #OUTER_LOOP_CURVE_TIME_01 | 0.04167 |
| #OUTER_LOOP_CURVE_TIME_02 | 0.08333 |
| #OUTER_LOOP_CURVE_TIME_03 | 0.125 |
| #OUTER_LOOP_CURVE_TIME_04 | 0.1667 |
| #OUTER_LOOP_CURVE_TIME_05 | 0.2083 |
| #OUTER_LOOP_CURVE_TIME_06 | 0.25 |
| #OUTER_LOOP_CURVE_TIME_07 | 0.29167 |
| #OUTER_LOOP_CURVE_TIME_08 | 0.3333 |
| #OUTER_LOOP_CURVE_TIME_09 | 0.375 |
| #OUTER_LOOP_CURVE_TIME_10 | 0.41667 |
| #OUTER_LOOP_CURVE_TIME_11 | 0.4583 |
| #OUTER_LOOP_CURVE_TIME_12 | 0.5 |
| #OUTER_LOOP_CURVE_TIME_13 | 0.54167 |
| #OUTER_LOOP_CURVE_TIME_14 | 0.5833 |
| #OUTER_LOOP_CURVE_TIME_15 | 0.625 |
| #OUTER_LOOP_CURVE_TIME_16 | 0.6667 |
| #OUTER_LOOP_CURVE_TIME_17 | 0.70833 |
| #OUTER_LOOP_CURVE_TIME_18 | 0.75 |
| #OUTER_LOOP_CURVE_TIME_19 | 0.79167 |
| #OUTER_LOOP_CURVE_TIME_20 | 0.8333 |
| #OUTER_LOOP_CURVE_TIME_21 | 0.875 |
| #OUTER_LOOP_CURVE_TIME_22 | 0.9167 |
| #OUTER_LOOP_CURVE_TIME_23 | 0.9583 |
| #OUTER_LOOP CURVE TIME_24 | 1.0 |

Outer_Loop_Misc_ Parms is an array of parameters which may be passed to the outer loop system 108 to make modifications in the algorithm, providing a method for making subtle adjustments to an algorithm for different tissue types or handsets.

A miscellaneous outer loop algorithm parameter table is for sub-variations within a specific algorithm structured as a two dimensional array, Outer_Loop_Misc_Parm[y][x].
OUTER_LOOP_MISC_PARMS_00_00 10.0

Pulse modes of the outer loop system 108 are programmed with the following exemplary commands:

Turning ON or OFF the pulse mode is accomplished with the commands:

| |
|---|
| #PULSE_MODE_ON |
| #PULSE_MODE_OFF |

Specifying the pulse on/off widths in seconds is accomplished with the commands:

| | | |
|---|---|---|
| #PULSE_ON_WIDTH | 0.100 | // 100 ms |
| #PULSE_OFF_WIDTH | 0.200 | // 200 ms |

The number of pulses to be delivered is specified by the command:

| | | |
|---|---|---|
| #NUM_PULSES | 5 | // 5 pulses |

The output level (in units of the inner loop desired output) is specified by the command:

| | | |
|---|---|---|
| #PULSE_OFF_LEVEL | 7 | // 7 watts if constant power |

III. Inner Loop System

The inner loop system 102 is responsible for the low level control of the RF delivery. The inner loop system 102 has programming controls for the control variable selection (e.g., current, power or voltage control), control curve definition (e.g., power curve shape), waveform definition, RF Frequency selection, calibration, sensor variable gain dynamics (e.g., automatic gain control dynamics for the V, I sensors 104) and control dynamics (e.g., PID variables for the control system).

The inner loop system 102 can be programmed for two basic modes of operation, open loop and closed loop. In open loop mode, the RF output is set to the fixed value of the high voltage power supply, and is not adjusted by software. The calibration of output RF power is controlled by Econ_Gain and Offset parameters, and the power curve is defined by the RF stage characteristics. In closed loop mode, the software reads the sensor board values of V, VI phase shift and I, and calculates Vrms, Irms, Pavg (which may be determined in accordance with the VI phase shift, Zrms, crest factor, cable impedances, Vpeak, and/or Ipeak and controls the RF output to match the desired control curve.

III.a. Command File Programming

Inner loop commands are typically specified in an 'Inner Loop' command file so that the commands are separate from the 'Outer Loop' and 'Meta' commands files. This configuration allows easier sharing of command file programming.

III.a.1. RF Frequency Selection

The system may have various RF frequency selections available such as: 250, 500, 750, 1000, 1250, 1500, 1750, 2000 Khz.

Exemplary command file programming commands for frequency selection are as follows:

```
#SET_FREQ_SEL_250KHZ
#SET_FREQ_SEL_500KHZ
#SET_FREQ_SEL_750KHZ
#SET_FREQ_SEL_1000KHZ
#SET_FREQ_SEL_1250KHZ
#SET_FREQ_SEL_1500KHZ
#SET_FREQ_SEL_1750KHZ
#SET_FREQ_SEL_2000KHZ
```

III.a.2. PID Parameters

The inner loop control dynamics are controlled by two sets of parameters, the PID parameters and the I, P, V gain adjusts. The PID parameters are adjusted to give the appropriate dynamic response assuming a system gain of 1. The I, P and/or V gain adjusts are used to modify the PID parameters based on the actual gains of the system in the respective control area (e.g., current, power and voltage) which changes based on load impedance, frequency, and waveform duty cycle.

Exemplary PID parameter commands are:

```
#CNTL_SYS_P 0.8269
#CNTL_SYS_I 0.7133
#CNTL_SYS_D 0.0264
```

Control system target gain compensation controls the change in loop gain based on which target the control system is aiming at (e.g., current, power, voltage). The PDD_GAIN_ADJ is multiplied by the PID values to change the loop gain, e.g., P CNTL_SYS_P*I_PID_GAIN_ADJ.

Exemplary Gain Adjust parameter commands are:

```
#I_PID_GAIN_ADJ 0.3
#P_PID_GAIN_ADJ 0.008
#V_PID_GAIN_ADJ 0.005
```

III.a.3. Crest Factor

Crest factor is defined as: Crest Factor=Pk/Rms. Crest factor specifies the ratio of the signal PK to RMS value, thus giving an indication of maximum amplitude to be expected from the waveform.

Since the system reads the actual V, I waveforms, the software needs to know how to set the scaling for sensors on a sensor board for the specified waveform. Crest factor allows the software to calculate the maximum expected amplitude of the waveform, so that it can calculate the PID settings for the sensor board.

The crest factor should be measured at about 10 ohms, which is typically the highest (e.g., corresponds to the least ringing).

An exemplary crest factor setting command is:
CREST_FACTOR 2

III.a.4. Control Mode/Curve Definitions

A control mode definition specifies which basic mode the control system operates in, open or closed loop.

Exemplary control mode definition commands are:

```
#CONTROL_MODE_IS_OPEN_LOOP
#CONTROL_MODE_IS_CLOSED_LOOP
```

A control curve definition specifies how the impedance curve maps are interpreted.

Exemplary control curve definition commands are:

```
#CONTROL_CURVE_IS_CURRENT
#CONTROL_CURVE_IS_POWER
#CONTROL_CURVE_IS_VOLTAGE
```

III.a.5. Control System Maximums

Control system maximum parameters control the maximum outputs allowed for the generator in the given mode. This protects the generator, as the control system does not allow the current, power, and/or voltage to go beyond these limits no matter what other settings are programmed to be set to. Current is in RMS Amps, power in watts, and voltage is in RMS volts.

Exemplary maximum parameter control commands are:

```
#MAX_CURRENT 4.0
#MAX_POWER   150
#MAX VOLTAGE 500
```

III.a.6. Control Curve Definition

An RF output control curve can be programmed to one of at least three modes of operation: constant current, constant power and constant voltage.

The modes of operation specify the target that the control system tries to control. All of these modes use two maps (e.g., the curve map and the impedance map) and the Zlow and Zhigh parameters to define the operation. Viewed together these two maps define the basic shape of the control curve at the specified impedance points. Preferably, the curve map is normalized from 0 to 1.0 and the impedance map is in ohms.

Exemplary maps can be viewed as below:

| Impedance Map Value | Curve Map Value |
| --- | --- |
| 0 | 0.5 |
| 100 | 0.75 |
| 200 | 1.0 |
| 300 | 1.0 |
| 500 | 0.5 |

A curve defined by the exemplary map value is shown in FIG. 2A. Exemplary charts of each mode are shown in FIGS. 2B-2D and explained below.

III.a.6.i. Constant Current Curves

The constant current mode attempts to provide constant current from 0 to Z High ohms. After Z High ohms, it switches to providing constant voltage (see FIG. 2B).

III.a.6.ii. Constant Power Curves

The constant power mode attempts to provide constant power from Z Low to Z High ohms. Below Z Low, it switches to providing constant current mode, and above Z High, it switches to providing constant voltage (see FIG. 2C).

III.a.6.iii. Constant Voltage Curves

The constant voltage mode attempts to provide constant voltage from Z Low and above. Below Z Low, it switches to providing constant current (see FIG. 2D).

III.a.7. Sensor Automatic Gain Control Dynamics

To accurately read the voltage and current sensors 104, an automatic gain control system is provided to the electrosurgical generator system 200 for providing a high speed A/D converter with a properly amplified signal. The dynamics of this gain control are programmed as a PID controller. The commands for programming the PID controller are as follows:

| | | |
|---|---|---|
| #V_SENSOR_VGAIN_P | 0.002 | //Voltage Var Gain P |
| #V_SENSOR_VGAIN_I | 0.004 | //Voltage Var Gain I |
| #V_SENSOR_VGAIN_D | 0.0 | //Voltage Var Gain D |
| #I_SENSOR_VGAIN_P | 0.002 | //Current Var Gain P |
| #I_SENSOR_VGAIN_I | 0.004 | //Current Var Gain I |
| #I_SENSOR_VGAIN_D | 0.0 | //Current Var Gain D |

III.a.8. Waveform Definition

The RF waveform is defined by a pulse generator which activates the main RF stage (e.g., FETs). The programming of the pulse generator allows specification of at least the pulse width, the number of pulses and an off time. This allows a wide variety of waveform patterns to be programmed for the electrosurgical generator system 200.

III.a.9. Outer Loop

One embodiment of the present disclosure includes splitting the outer loop system into two sub-sections: an outer loop target generator which handles the time-based changes to the setpoint of the outer loop (e.g., temperature versus time curves) and an inner loop target generator which selects which target (e.g., voltage, current, power) the inner loop is controlling.

III.a.10 Downloading Configuration Files

It is contemplated that the system of the present disclosure can be configured such that the system allows the downloading of the configuration files into the electrosurgical generator by the user. The new configuration files could be purchased or given to the user for upgrading the electrosurgical system.

Figure 3:
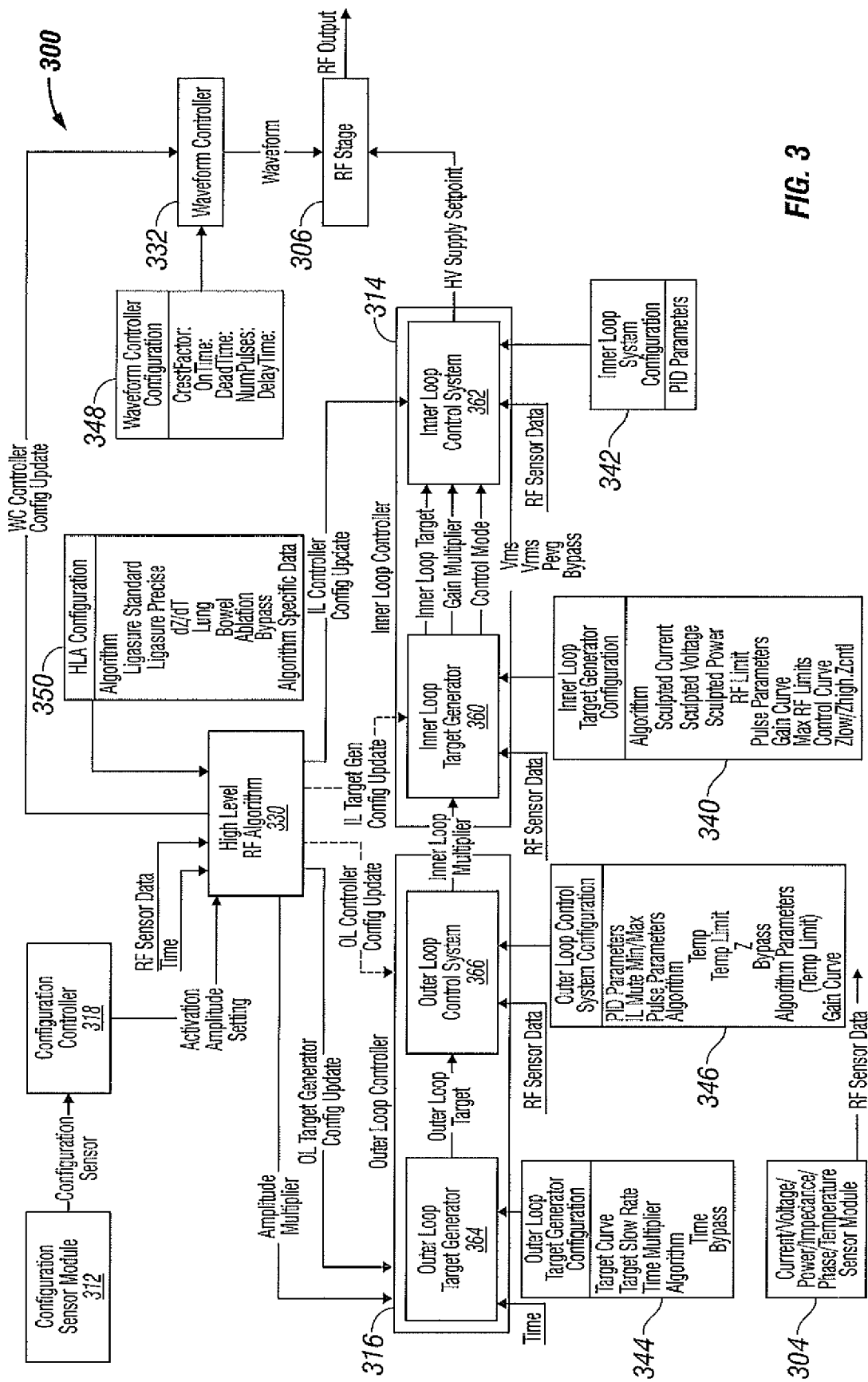
FIG. 3 is a block diagram of a control loop system of an electrosurgical generator in accordance with another embodiment of the invention.

FIG. 3 shows another embodiment of the electrosurgical generator system, designated generally by the number 300. An inner loop controller 314 includes at least the functionality of the inner loop controller 114 shown in FIG. 1. An outer loop controller 316 together with a high level RF algorithm (HLA) module 330 include at least the functionality of the outer loop controller 116 shown in FIG. 1. A control system for an electrosurgical generator having an inner and outer loop controller is described in U.S. patent application Ser. No. 10/427,832, filed on May 1, 2003, the contents of which are incorporated herein by reference in their entirety. A configuration controller 318 includes at least the functionality of the configuration controller 118 shown in FIG. 1. A sensor module 304 includes at least the sensors 104 shown in FIG. 1 and a configuration sensor module 312 includes at least the sensors 112 shown in FIG. 1. An RF stage 306 corresponds to the RF stage 106 shown in FIG. 1. A waveform pattern controller 332 provides at least functionality described above with respect to waveform generation.

Configuration data 340, 342, 344, 346, 348, 350 is generated by the configuration controller 318. The inner loop controller 314 includes an inner loop target generator (ILTG) 360 and an inner loop control module (ILCM) 362. The outer loop controller 316 includes an outer loop target generator (OLTG) 364 and an outer loop control module (OLCM) 366. The ILTG configuration data 340 is provided to the ILTG 360. The ILCM configuration data 342 is provided to the OLCM 366. The OLTG configuration data 344 is provided to the OLTG 364, the OLCM configuration data 346 is provided to the OLCM 366. The waveform controller configuration data 348 is provided to the waveform controller 332. The HLA module configuration data 350 is provided to the HLA module 330.

The elements ILTG 360, ILCM 362, OLTG 364, OLCM 366, the configuration controller 318, the configuration sensor module 312, the HLA module 330, the waveform controller 332 or the sensor module 304, or a combination thereof, may be disabled and/or bypassed, or a connection between two or more elements may be disabled so that the electrosurgical generator control system 300 may operate without the disabled element. The disabled elements pass the input directly to the output of the module, thus allowing the enabled elements to operate with no change from the disabled units. The inner loop controller 314 processes sensor data received from the sensor module 304 in accordance with configuration data received from the configuration controller 318, updated configuration data received from the HLA module 330, and the inner loop multiplier control signal received from the outer loop controller 316, and generates a supply setpoint control signal which is provided to the RF stage 306, where an amplitude of an aspect of the RF energy output by the RF stage 306 is controlled in accordance with the supply setpoint. In the example provided in FIG. 3, the supply setpoint is an HV supply setpoint which controls amplitude of the voltage output by the RF stage 306.

The ILTG 360 receives configuration data including at least one algorithm selected from algorithms including a sculpted curve (including sculpted current, sculpted voltage and sculpted power) and RF limit algorithms, pulse parameters (pulse enable (for enabling or disabling pulsing function), pulse on (length of "high" pulse), pulse off (length of "low" pulse), pulse min (amplitude of "low" pulse), an inner loop gain curve, maximum RF limits, a control curve and Zlow, Zhigh, Zcntl values (where Zcntl indicates when to switch the control variable, e.g., from current to voltage, or vice versa); sensor data from the sensor module 304; and the inner loop multiplier from the outer loop controller 316. The ILTG 360 generates a target signal to the ILCM 362 based on the inner loop control curve provided via the configuration data from the configuration controller 318 and updateable by the configuration update data from the HLA module 330; the inner loop multiplier from the outer loop controller 316; and impedance and actual RF current and voltage from the sensor module 304. The target signal preferably represents voltage, but it can also represent the HV supply setpoint in the case when the ILCM is bypassed and/or disabled.

The ILTG 360 further includes modules for performing the following functions: performing a sculpted curve algorithm including, for example, but not limited to converting a sculpted current or power control curve into a voltage control curve; limiting the control curve to the maximum values (e.g., for current, voltage and power) allowed for the hardware; calculating and generating the inner loop target based on the sensor data, the control curve and the inner loop multiplier; controlling the inner loop control module gains based on impedance sensor data and the gain curve which specifies changes in gain due to changes in impedance for generating the gain multiplier; pulsing the inner loop target; and selecting a mode based on the sensed load impedance and the impedance breakpoints Zlow, Zhigh and Zcntl, and generating a control mode signal in accordance with the selected mode.

Mode selection determines which sensor data is to be used by the ILCM 362 and which variable is to be controlled, e.g., sensor data that corresponds to current, voltage or power for controlling current, voltage or power, respectively. Preferably, current control is to be used for impedances less than Zlow, power or voltage control is used for impedance values between Zlow and Zhigh, and voltage control is used for the remaining impedance values. To avoid inaccuracy and prevent unnecessary control mode switching when the impedance is near a breakpoint, hysteresis is used when the impedance is close to a breakpoint.

The RF limit algorithm causes the ILTG 360 and the ILCM 362 to operate in an open loop mode in which there is minimal software control of the HV supply setpoint output in response to sensor data. The open loop mode is generally used for calibration and service functions, but is not limited thereto. Preferably, in the open loop mode the amplitude activation setting determines the percentage of full scale output that the RF stage 306 will deliver. The RF limit algorithm protects the RF stage 306 from user actions, such as setting the activation amplitude setting to a level that could cause the HV supply setpoint to be set to a level that could damage the RF stage 306. The HV supply setpoint is kept within predetermined limits, where the limits are determined by the control curve.

The inner loop control curve is interpreted to represent the maximum allowed HV supply setpoint at the specified impedance (Z). As long as the maximum HV supply setpoint allowed is not exceeded, as defined by the inner loop control curve, control of the HV supply setpoint is based on the inner loop multiplier. If the control curve is exceeded, then the output HV supply setpoint is held at the maximum allowed HV supply setpoint for providing protection to the electrosurgical unit receiving the energy generated by the RF stage 306. The HV supply setpoint is set to equal the inner loop multiplier after the HV supply setpoint is less than the maximum RF limit value, with some possible hysteresis.

The max RF limits parameter provides another layer of control layered on top of the control curve for use with any algorithm by providing maximum limits for current, voltage and/or power levels of the HV supply setpoint. The control layer which uses the max RF limits parameter further provides protection to the RF stage unit 306 and the electrosurgical unit (ESU) receiving the energy generated by the RF stage 306, including protection from changes to the software. Furthermore, the control system may use the minimum of the limits described by the control curve and the max RF limit for limiting the HV supply setpoint.

The pulsing function may run in parallel with other ILTG 360 algorithms. The duration of the "high" and "low" pulses, the time between leading edges, the level for the "low" pulse, etc., are specified by the pulse parameters. The level for the "high" pulse is defined by the control curve, the impedance data from the sensor data and the inner loop multiplier for closed loop control, or by the inner loop multiplier for open loop control, such as when the RF limit algorithm is performed. The pulsing of the inner loop target may contribute to providing sharp edged pulses of the HV supply setpoint, if desired.

The inner loop control curve received via the configuration data specifies the inner loop desired output values versus sensed impedance values obtained from sensor data. The desired output values of the received inner loop control curve represent current, voltage or power, as determined by the algorithm received via the configuration data (e.g., the sculpted current, voltage or power algorithm, respectively). The received inner loop control curve may be converted into a voltage, current or power curve, in accordance with the mode selected, in which the desired output values represent voltage, current or power, respectively. The control curve (or converted control curve) may be structured, for example, as a multi-dimensional array. One column of the array specifies impedance values, and another column specifies desired output values, where the desired output values represent current, power or voltage in accordance with the control mode. Preferably the desired output values are normalized between 0 and 1.0. A desired output value which is output as the inner loop target is generated by obtaining a normalized desired output value via linear interpolation based on the actual impedance, and multiplying the normalized desired output value by the inner loop multiplier.

Control of the inner loop control module gains (herein referred to as inner loop gain control) includes generating the gain multiplier in response to a constant control voltage as impedance changes. System gain (e.g., RF voltage/HV supply set-point, where the RF voltage is measured RF voltage output by the RF stage 306) varies with patient load impedance. The inner loop gain control objective is to stabilize the system gain to keep it close to constant as the load impedance changes. The inner loop gain curve is theoretically a set of points of a gain multiplier plotted versus impedance derived from the design of the hardware, which is designed to adjust the gains due to the response of the electrosurgical generator system 300.

The gain curve preferably holds a normalized voltage response versus impedance. By using a normalized voltage response, the voltage is converted into the variable that we are controlling (current, power, or voltage). The gain multiplier is computed by taking the inverse of the voltage response that corresponds to the sensed impedance. The gain multiplier is used to adjust the inner loop PID values of the ILCM 362 so that the control system gain is close to constant. Accordingly, the PID values should be calculated assuming a system gain of 1.0, as the PID values are adjusted as described above.

To compute the gain multiplier, for voltage control, the interpolated value of the gain curve is inverted. For power control, the gain multiplier is $Z/V^2$ (where V is the interpolated value from the gain curve). For current control, the gain multiplier is $Z/V$. Accordingly, the ILSM 362 can use a single set of PID gain values for the inner loop voltage, current or power control, and the gain multiplier is used to modify the PID gains during the procedure in virtual real-time.

The ILCM 362 receives configuration data including control parameters, such as PID parameters; sensor data from the sensor module 304 and the inner loop target, the gain multiplier and the control mode (Irms, Vrms, Pavg or Bypass) from ILTG 360. The ILCM 362 adjusts the HV supply setpoint in accordance with the received data so that the inner loop target is reached.

The ILCM 362 preferably uses a control algorithm, such as a PID algorithm, which is able to switch between control modes such as current control, voltage control, power control and a bypass mode (e.g., minimal control, where received data is provided as the output) without large disturbances when switching control modes. When the ILTG 360 is performing the RF limit algorithm, the ILCM 362 is preferably in bypass mode. When switching between control modes, the PID loop algorithm (if active) pre-loads the integral term for minimum disturbance.

With respect to the outer loop controller 316, the OLTG 364 receives configuration data including the outer loop target curve, the target slew rate, the time multiplier and an algorithm selectable from algorithms including time control or bypass algorithms; the amplitude multiplier from the HLA module 330; and time signals. Other than when performing the bypass algorithm, the OLTG 364 generates a time varying outer loop target in accordance with the received data which is provided to the OLCM 366, where the outer loop target may represent a property such as, but not limited to, temperature, current, power, voltage or impedance. Preferably, the outer loop target is generated by a linear interpolation of the adjusted outer loop target curve, where the target curve provided via the OLTG configuration data is adjusted in accordance with the amplitude multiplier, the time multiplier and/or time.

The outer loop target slew rate parameter allows the system to have a programmable slew rate of the outer loop target, so that regardless of how quickly the amplitude multiplier changes, the outer loop target will not change faster than the programmed slew rate. The outer loop target slew rate control function is typically used in systems in which the user may have direct control of a parameter, such as the activation amplitude setting, and it is desired to limit the rate at which the activation amplitude setting can be changed.

The OLCM 366 receives configuration data including control parameters, such as PID parameters, inner loop multiplier maximum and minimum limit values, pulse parameters, at least one algorithm selectable from algorithms such as temperature, temperature limit, impedance (Z), or bypass algorithms, algorithm parameters, such as temperature limits and an outer loop gain curve; sensor data from the sensor module 304 and the outer loop target from the OLTG 364. Preferably, the OLCM 366 uses a control algorithm, such as a PID algorithm which operates in accordance with the PID parameters. The OLCM 366 adjusts the inner loop multiplier in accordance with the received data in order to reach the outer loop target.

The OLCM 366 is capable of pulsing the inner loop multiplier. When the pulse is "on", the output value is the computed inner loop multiplier. When the pulse is "off", the output is set to a predetermined value.

The OLCM 366 controls outer loop gain. The outer loop gain curve describes a plot of gain multiplier versus impedance derived from the inner loop control curve, and thus the programming of the inner loop by way of the configuration parameters. The outer loop gain curve may be structured, for example, as a two-dimensional array. When outer loop gain control is enabled, the outer loop gain is multiplied by the gain multiplier that corresponds to the received impedance sensor data. The outer loop gain control stabilizes the system gain to maintain system gain that is close to constant. From the perspective of the outer loop controller 316, the system gain varies with patient load impedance due to the inner loop control curve programming. Conceptually, the outer loop gain is multiplied by the inverse of the normalized inner loop control curve, thus keeping the system gain close to constant. The outer loop gain curve specifies the inverse of the normalized inner loop control curve, where the outer loop gain curve may be further adjusted for keeping the system stable.

The HLA module 330 receives configuration data including at least one procedural algorithm selectable from algorithms for controlling the electrosurgical generator system 300 during specific types of procedures, or procedures performed under specific conditions, such as on specific organs. The procedural algorithms include algorithms, such as, vessel sealing (e.g., LigaSure™ (standard and precise)), rate of change of impedance (dZ/dt), lung, bowel, ablation, etc., and bypass algorithms, and a combination thereof; algorithm specific data for adjusting at least one specified procedural algorithm; sensor data from the sensor module 304; time signals; user entered settings; and the activation amplitude setting from the configuration controller 318.

Preferably, the HLA module 330 uses a state based control algorithm. The HLA module 330 performs top level RF delivery algorithms which are primarily state based. The HLA module 330 has the capability of changing the configuration data of the lower level modules, including the ILTG 360, the ILCM 362, the OLTG 364 and the OLCM 366 and the waveform controller (332). The HLA module 330 sets up the lower level modules in accordance with the received data by adjusting the corresponding configuration data as determined necessary. Furthermore, during a procedure the HLA module 330 reprograms the lower level modules in accordance with the received data by adjusting the corresponding configuration data in accordance with the algorithm selected, and in response to measured properties as indicated by the received sensor data, where the reprogramming may be performed in virtual real-time.

The user entered settings may be used in conjunction with any of the algorithms selected. Furthermore, the user entered settings may control the activation amplitude setting for one or more electrical or physical properties (e.g., power, current, voltage or temperature) without directly identifying the particular property and target setting. For example, the user may select from a variety of generic settings, where each generic setting includes a predetermined setting for one or more properties.

The waveform controller 332 receives configuration data including "on" time, dead time, number of pulses per burst of pulses, and delay time between bursts of pulses. It is contemplated that the waveform controller 332 may be programmed by the HLA module 332 if determined necessary, and/or by the configuration file via download from the configuration controller 318. The waveform controller 332 controls the hardware which generates a wave pattern (such as a square wave pattern) which drives FETs in the RF stage. Parameters of the waveform pattern that may be controlled by the waveform controller 332 include at least, "on" time (pulse width of a single pulse), dead time (delay to next pulse), number of pulses per group of pulses, and delay time between groups of pulses.

The waveform generator 332 may receive an amplitude envelope parameter with the configuration parameters, and may further include circuitry, such as analog and/or logic circuitry for adjusting amplitude of pulses within a burst of pulses. The amplitude envelope parameter may describe the amplitude setting for individual pulses of groups (or bursts) of pulses. The amplitude adjustments may be performed at a rate that is faster than the rate at which the software, such as the inner loop controller 314, is capable of providing control, so that the amplitude adjustments may be provided for individual pulses of groups of pulses. The waveform generator may receive a control signal, such as a control signal from the ILCM 362, indicative of the HV supply setpoint, for synchronizing the amplitude adjustments with the HV supply setpoint or with the signals output by the RF stage 106.

Preferably, the configuration controller 318 is a system which selects the required configuration files based on user input and download them to the rest of the system. It is contemplated that the configuration controller 318 may be removable and replaceable. The configuration controller receives configuration sensor data from the configuration sensor module 312 and/or user input devices (not shown) for direct user input. The configuration controller 318 generates the configuration data and the activation amplitude setting in accordance with the received data. The configuration controller 318 selects the algorithm to be used by the ILTG 360, OLTG 364, OLCM 366 and the HLA 330. The configuration data is provided to the appropriate modules as described above, and the activation amplitude setting is provided to the HLA module 330.

The configuration controller may configure itself (or alternatively be configured by another processor) in accordance with conditions, such as the ESU and/or the user interface to the electrosurgical generator system being used.

The configuration sensor module 312 includes sensors for sensing user actions, (including user actions not intentionally related to providing input to the configuration controller 318), environmental conditions, patient conditions or other properties or conditions. The configuration sensor module 312 further includes analog and or digital circuitry and software modules for processing signals generated by the sensors such as for preparing the signals for input to the configuration controller 318, and for controlling the sensors.

The sensors of the configuration sensor module 312 may include, for example, a sensor for sensing adjustment of a slider mechanism on the ESU for selecting a parameter on the ESU, an optical sensor for sensing a property of the patient's tissue, a proximity sensor for sensing thickness of the patient's tissue, a motion sensor for sensing motion of the ESU or the patient, a sensor for sensing moisture levels of tissue, etc. A portion of the sensors may be provided within the sterile field of the electrosurgical procedure. The configuration sensor module 312 may further include one or more commercially available user input devices.

The sensor module 304 includes sensors for sensing electrical properties of energy as output by the electrosurgical device, and/or electrical and/or physical properties proximate the surgical site or the ESU. Furthermore, the sensor module includes analog and or digital circuitry and software modules for processing signals generated by the sensors such as for preparing the signals for input to the control system of the electrosurgical generator system 300, and for calculating values derived from the sensed properties. It is contemplated that sensors and circuitry may be shared by the sensor module 304 and the configuration controller 318. Furthermore, the sensor module 304 may further include at least one control system for controlling the sensors, amplification of sensed signals, sampling rates of the sensors, etc. The sensor module 304 may further include one or more commercially available user input devices.

In a preferred embodiment, a user may enter user input to the configuration controller for selecting (directly or indirectly) configuration parameters, the activation amplitude setting and the amplitude multiplier. As described above, the user input to the configuration controller may not be intentionally entered for selecting configuration parameters.

It is contemplated that another configuration parameter, an expected crest factor parameter, may be provided to at least one of the modules of the control system of the electrosurgical generator 300 for providing further control. Furthermore, the sensor module 304 may include sensors for sensing the crest factor. The control system may further include a safety monitor module which compares the expected crest factor parameter with the sensed crest factor, and sends control signals to other modules of the control system for making adjustments in accordance with the results of the comparison. The sensor module 304 may configure the sensors for setting up the dynamic range of the sensors in accordance with the expected crest factor parameter.

It is further contemplated that the control system includes an activation sequencer which controls startup and ending of RF delivery. The activation sequencer may receive configuration data from the configuration controller 318 and or updated configuration data from the HLA module 330 for performing startup and/or shutdown procedures in accordance with the configuration data and/or updated configuration data.

The software modules of the electrosurgical generator control system 300, including the inner loop controller 314, outer loop controller 316, the configuration controller 318, the HLA module 330, the waveform controller 332 and control modules associated with the sensor module 304 and/or the configuration sensor module 312 are respectively executable on at least one processor, such as a microprocessor and/or a DSP. Resources for processing, storage, etc., or a combination thereof may be shared by any combination of the aforementioned software modules. The software instructions of the respective software modules may be stored on computer readable medium, such as CD-ROMs or magnetic disks, and/or may be transmitted and/or received via propagated signals.

In operation, the control system may be initialized during the power up and/or the activation process. The electrosurgical generator system 300 recognizes (via sensing or "plug and play" notification) the type of ESU and/or electrosurgical generator user interface to be used. Sensors of the sensor module 304 and/or the configuration sensor module 312 sense initialization properties associated with the environment, ESU or patient. Information is entered via a user interface, such as patient and/or procedure related information (procedure to be performed, tissue to be operated upon, patient identification, age, weight, expected fat content). The information or additional information may be retrieved from a database accessible by the control system of the electrosurgical generator system 300.

The appropriate configuration files are selected or generated by the configuration controller 318. It is contemplated that at least a portion of the configuration files are stored by the configuration controller 318 and/or associated memory. Accordingly, selected configuration files not stored by the configuration controller 318 may be downloaded to the configuration controller 318 through various methods. Upon activation of the electrosurgical generator system 300 the configuration controller 318 downloads the configuration files into the respective modules of the control system.

The control system for the electrosurgical generator system 300 provides a high degree of flexibility for performing a wide variety of different types of control for controlling the output of electrosurgical energy for use in a wide variety of types of procedures which may be performed under a wide variety of circumstances. Furthermore, the control system provides a wide variety of different types of control during a procedure, where the control and selection of the type of control is provided on the fly, or in virtual real time in response to properties associated with sensed properties and/or user input or actions. The type of control provided may be selected in response to a variety of factors, such as sensed or input tissue response, type of electrosurgical instrument being used, patient profile, the type of procedure being performed, environmental conditions, the type of tissue being treated and the condition of the tissue being treated.

Although this disclosure has been described with respect to preferred embodiments, it will be readily apparent to those having ordinary skill in the art to which it appertains that changes and modifications may be made thereto without departing from the spirit or scope of the claims appended hereto.

What is claimed is:

1. An electrosurgical generator system having an RF stage for outputting at least one waveform of electrosurgical energy for performing an electrosurgical procedure, the electrosurgical generator comprising:

at least one control module executable on at least one processor for controlling in combination at least one parameter of the output electrosurgical energy;

a configuration controller for generating configuration data including configuration data for respective control modules of the at least one control module and providing the corresponding configuration data to the respective control modules for configuring the respective control modules to provide a type of control selectable from a variety of types of control;

a sensor module having at least one sensor that senses electrical or physical properties relating to the output electrosurgical energy or the application of the electrosurgical energy and generates sensor data corresponding thereto;

wherein the at least one control module includes:

an outer loop controller that generates a control signal in accordance with at least a first subset of the sensor data; and an inner loop controller that generates a setpoint control signal and provides the setpoint control signal to the RF stage for controlling at least an amplitude of the energy output by the RF stage, wherein the setpoint control signal is generated based on at least the control signal generated by the outer loop controller and a second subset of the sensor data;

wherein the outer loop controller includes:

an outer loop target generator that generates an outer loop target value based on at least a time signal indicative of a time lapse during the procedure and an outer loop target curve providing target values versus time values provided via the configuration data; and an outer loop control module performing a control algorithm for generating the control signal based on at least the outer loop target value and the first subset of sensor data;

wherein the inner loop controller includes:

an inner loop target generator that generates an inner loop target value based on at least the second subset of sensor data or an inner loop target curve providing target values versus impedance values provided via the configuration data; and an inner loop control module performing a control algorithm that generates the setpoint control signal based on at least the inner loop target value and the second subset of sensor data.

2. The electrosurgical generator system as in claim 1, wherein the at least one sensor is selected from the group consisting of current, phase shift, voltage, power, impedance, and temperature sensors.

3. The electrosurgical generator system as in claim 1, wherein the electrosurgical generator system further comprises a configuration sensor module having at least one sensor for sensing at least one property relating to at least one of a user action relating directly to operation of an electrosurgical instrument, and at least one of a physical or electrical property sensed in a field of the procedure, wherein the configuration sensor module generates at least one signal corresponding to the sensing.

4. The electrosurgical generator system as in claim 1, wherein the configuration data provided to the inner loop controller includes at least one of an algorithm selected from at least a sculpted current algorithm, a sculpted voltage algorithm and a sculpted power algorithm; pulse parameters for controlling a waveform pattern of the setpoint control signal; a gain curve providing predetermined gain multiplier values plotted versus predetermined impedance values; maximum limitation values for the setpoint control signal; a control curve providing target values plotted versus impedance values; predetermined impedance breakpoint values; and control algorithm parameters; and wherein the configuration data provided to the outer loop controller includes at least one of a target curve providing target values plotted versus time values; a target slew rate for limiting the slew rate of the outer loop controller; a time multiplier for adjusting the target curve with respect to the time values; control algorithm parameters; threshold range values for the control signal generated by the outer loop controller; pulse parameters for pulsing the control signal; an outer loop algorithm selected from at least one of a temperature algorithm, a temperature limit algorithm, and an impedance algorithm; outer loop algorithm parameters; and a gain curve providing predetermined gain multiplier values plotted versus predetermined impedance values.

5. The electrosurgical generator system as in claim 1, further comprising a waveform controller receiving configuration data from the configuration controller and controlling a waveform pattern of the electrosurgical energy generated by the RF stage.

6. The electrosurgical generator system as in claim 1, wherein each of the outer loop target generator, the outer loop control module, the inner loop target generator and the inner loop control module are bypassable.

7. The electrosurgical generator system as in claim 1, wherein the electrosurgical generator system further comprises a high level RF algorithm module for generating updated configuration data for at least one of the respective control modules in response to at least one of received sensor data and time signals indicative of the amount of time lapsed during a procedure, and providing the updated configuration data to the at least one of the respective control modules for reconfiguring the respective control modules.

8. The electrosurgical generator system as in claim 7, wherein the configuration data provided to the high level RF algorithm module includes at least an algorithm selection and algorithm specific data for adjusting at least one procedural algorithm.

\* \* \* \* \*